(12) United States Patent
Birk et al.

(10) Patent No.: US 8,900,118 B2
(45) Date of Patent: Dec. 2, 2014

(54) DOME AND SCREW VALVES FOR REMOTELY ADJUSTABLE GASTRIC BANDING SYSTEMS

(71) Applicant: Apollo Endosurgery, Inc., Austin, TX (US)

(72) Inventors: Janel A. Birk, Oxnard, CA (US); Robert E. Hoyt, Jr., Santa Barbara, CA (US); Sean Snow, Carpinteria, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 0 days.

(21) Appl. No.: 13/894,955

(22) Filed: May 15, 2013

(65) Prior Publication Data

US 2013/0253262 A1 Sep. 26, 2013

Related U.S. Application Data

(63) Continuation of application No. 12/712,952, filed on Feb. 25, 2010, now abandoned, which is a continuation-in-part of application No. 12/603,058, filed on Oct. 21, 2009, now Pat. No. 8,366,602.

(60) Provisional application No. 61/107,576, filed on Oct. 22, 2008.

(51) Int. Cl.
*A61F 2/00* (2006.01)
*A61F 13/00* (2006.01)
*A61F 5/00* (2006.01)

(52) U.S. Cl.
CPC .............. *A61F 5/0059* (2013.01); *A61F 5/0066* (2013.01); *A61F 5/0056* (2013.01)
USPC ............. 600/37; 128/897; 128/898; 128/899; 251/129.06; 251/129.17; 251/331; 251/335.2; 251/61.2; 251/61; 251/341; 251/346; 251/347; 137/414; 137/863; 604/237

(58) Field of Classification Search
USPC .................... 251/129.06, 129.17, 331, 335.2, 251/129.01, 61.1, 61, 61.2, 241, 346, 347; 600/37; 137/414, 863; 261/DIG. 68; 604/237; 128/897–899
See application file for complete search history.

(56) References Cited

U.S. PATENT DOCUMENTS 1,174,814 A 3/1916 Brennan
1,830,947 A 11/1931 Klingel
(Continued)

FOREIGN PATENT DOCUMENTS

CA 949965 6/1974
CN 1250382 A 4/2000
(Continued)

OTHER PUBLICATIONS

'Innovative medical devices and implants'; LGSP medical futures, p. 5.
(Continued)

*Primary Examiner* — Christine Matthews
*Assistant Examiner* — Sunita Reddy
(74) *Attorney, Agent, or Firm* — Gordon & Jacobson, PC

(57) ABSTRACT

An implantable device controls the movement of fluid to an inflatable portion of a gastric band. The implantable device includes a body. The body has an inlet, an outlet and a valve seat positioned between the inlet and the outlet. The body defines a fluid passage from the inlet to the outlet. The implantable device also includes a diaphragm. The diaphragm has one or more edges coupled to the body. The diaphragm is made of an elastomeric material and capable of being moved between a closed position that blocks the valve seat and does not allow the fluid to move from the inlet to the outlet and an open position that does not block the valve seat and allows the fluid to move from the inlet to the outlet.

9 Claims, 8 Drawing Sheets

(56) References Cited

U.S. PATENT DOCUMENTS

| | | |
|---|---|---|
| 2,013,025 A | 4/1934 | Bottoms |
| 1,999,683 A | 4/1935 | Borresen |
| 2,163,048 A | 6/1939 | McKee |
| 2,339,138 A | 1/1944 | Black |
| 2,405,667 A | 8/1946 | Andrew |
| 2,438,231 A | 3/1948 | Schultz |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck |
| 3,189,961 A | 6/1965 | Heller |
| 3,667,081 A | 6/1972 | Burger |
| 3,840,018 A | 10/1974 | Heifetz |
| 3,955,834 A | 5/1976 | Ahlrot |
| 4,053,176 A | 10/1977 | Hilbush |
| 4,117,727 A | 10/1978 | Friswell |
| 4,118,805 A | 10/1978 | Reimels |
| 4,133,315 A | 1/1979 | Berman |
| 4,157,713 A | 6/1979 | Clarey |
| 4,176,412 A | 12/1979 | Peterson |
| 4,236,521 A | 12/1980 | Lauterjung |
| 4,271,827 A | 6/1981 | Angelchik |
| 4,286,584 A | 9/1981 | Sampson |
| 4,299,012 A | 11/1981 | Oetiker |
| 4,340,083 A | 7/1982 | Cummins |
| 4,370,982 A | 2/1983 | Reilly |
| 4,399,809 A | 8/1983 | Baro |
| 4,406,656 A | 9/1983 | Hattler |
| 4,408,597 A | 10/1983 | Tenney |
| 4,417,567 A | 11/1983 | Trick |
| 4,424,208 A | 1/1984 | Wallace |
| 4,442,153 A | 4/1984 | Meltsch |
| 4,450,375 A | 5/1984 | Siegal |
| 4,485,805 A | 12/1984 | Foster |
| 4,492,004 A | 1/1985 | Oetiker |
| 4,551,862 A | 11/1985 | Haber |
| 4,558,699 A | 12/1985 | Bashour |
| 4,559,699 A | 12/1985 | Owen |
| 4,582,640 A | 4/1986 | Smestad |
| 4,582,865 A | 4/1986 | Balazs |
| 4,592,339 A | 6/1986 | Kuzmak |
| 4,592,355 A | 6/1986 | Antebi |
| 4,601,713 A | 7/1986 | Fuqua |
| 4,603,699 A | 8/1986 | Himpens |
| 4,667,672 A | 5/1987 | Romanoski |
| 4,671,351 A | 6/1987 | Rappe |
| 4,693,695 A | 9/1987 | Cheng |
| 4,694,827 A | 9/1987 | Weiner |
| 4,696,288 A | 9/1987 | Kuzmak |
| 4,708,140 A | 11/1987 | Baron |
| 4,716,154 A | 12/1987 | Maelson |
| 4,753,086 A | 6/1988 | Schmidt |
| 4,760,837 A | 8/1988 | Petit |
| 4,803,075 A | 2/1989 | Wallace |
| 4,858,619 A | 8/1989 | Toth |
| 4,872,483 A | 10/1989 | Shah |
| 4,881,939 A | 11/1989 | Newman |
| 4,883,467 A | 11/1989 | Franetzki |
| 4,886,787 A | 12/1989 | de Belder et al. |
| 4,896,787 A | 1/1990 | Delamour |
| 4,915,690 A | 4/1990 | Cone |
| 4,919,650 A | 4/1990 | Feingold |
| 4,925,446 A | 5/1990 | Garay |
| 4,944,487 A | 7/1990 | Holtermann |
| 4,944,659 A | 7/1990 | Labbe |
| 4,958,791 A | 9/1990 | Nakamura |
| 4,969,899 A | 11/1990 | Cox |
| 4,989,756 A | 2/1991 | Kagamihara |
| 4,994,019 A | 2/1991 | Fernandez |
| 5,045,060 A | 9/1991 | Melsky |
| 5,074,868 A | 12/1991 | Kuzmak |
| 5,084,061 A | 1/1992 | Gau |
| 5,089,019 A | 2/1992 | Grandjean |
| 5,091,171 A | 2/1992 | Yu |
| 5,116,652 A | 5/1992 | Alzner |
| 5,120,313 A | 6/1992 | Elftman |
| 5,143,724 A | 9/1992 | Leshchiner |
| 5,152,770 A | 10/1992 | Bengmark |
| 5,160,338 A | 11/1992 | Vincent |
| 5,188,609 A | 2/1993 | Bayless |
| 5,224,494 A | 7/1993 | Enhorning |
| 5,226,429 A | 7/1993 | Kuzmak |
| 5,246,456 A | 9/1993 | Wilkinson |
| 5,246,698 A | 9/1993 | Leshchiner |
| 5,259,399 A | 11/1993 | Brown |
| 5,277,333 A | 1/1994 | Shimano |
| 5,318,533 A | 6/1994 | Adams |
| 5,326,349 A | 7/1994 | Baraff |
| 5,343,894 A | 9/1994 | Frisch |
| 5,356,883 A | 10/1994 | Kuo |
| 5,360,445 A | 11/1994 | Goldowsky |
| 5,383,858 A | 1/1995 | Reilly |
| 5,391,156 A | 2/1995 | Hildwein |
| 5,399,351 A | 3/1995 | Leshchiner |
| 5,425,716 A | 6/1995 | Kawasaki |
| 5,449,363 A | 9/1995 | Brust |
| 5,449,368 A | 9/1995 | Kuzmak |
| 5,458,568 A | 10/1995 | Racchini |
| 5,496,312 A | 3/1996 | Klicek |
| 5,496,313 A | 3/1996 | Gentelia |
| 5,509,888 A | 4/1996 | Miller |
| 5,531,716 A | 7/1996 | Luzio |
| 5,535,752 A | 7/1996 | Halperin |
| 5,554,113 A | 9/1996 | Novak |
| 5,562,714 A | 10/1996 | Grevious |
| 5,569,839 A | 10/1996 | Ajot |
| 5,601,604 A | 2/1997 | Vincent |
| 5,607,418 A | 3/1997 | Arzbaecher |
| 5,633,001 A | 5/1997 | Angstrom |
| 5,649,546 A | 7/1997 | Steinbeck |
| 5,653,718 A | 8/1997 | Yoon |
| 5,658,298 A | 8/1997 | Vincent |
| 5,669,416 A | 9/1997 | Nusche |
| 5,676,162 A | 10/1997 | Larson |
| 5,681,284 A | 10/1997 | Herskowitz |
| 5,695,504 A | 12/1997 | Gifford |
| 5,704,893 A | 1/1998 | Timm |
| 5,713,911 A | 2/1998 | Racenet |
| 5,733,257 A | 3/1998 | Sternby |
| 5,741,232 A | 4/1998 | Reilly |
| 5,748,200 A | 5/1998 | Funahashi |
| 5,758,667 A | 6/1998 | Slettenmark |
| 5,759,015 A | 6/1998 | Van Lintel et al. |
| 5,766,232 A | 6/1998 | Grevious |
| 5,769,877 A | 6/1998 | Barreras |
| 5,785,295 A | 7/1998 | Tsai |
| 5,795,333 A | 8/1998 | Reilly |
| 5,807,311 A | 9/1998 | Palestrant |
| 5,808,203 A | 9/1998 | Nolan |
| 5,817,113 A | 10/1998 | Gifford |
| 5,827,529 A | 10/1998 | Ono |
| 5,833,698 A | 11/1998 | Hinchliffe |
| 5,861,014 A | 1/1999 | Familoni |
| RE36,176 E | 3/1999 | Kuzmak |
| 5,886,042 A | 3/1999 | Yu |
| 5,891,089 A | 4/1999 | Katz |
| 5,904,697 A | 5/1999 | Gifford |
| 5,910,149 A | 6/1999 | Kuzmak |
| 5,928,195 A | 7/1999 | Malamud |
| 5,938,669 A | 8/1999 | Klaiber |
| 5,944,696 A | 8/1999 | Bayless |
| 5,944,751 A | 8/1999 | Laub |
| 5,993,473 A | 11/1999 | Chan |
| 5,997,502 A | 12/1999 | Reilly |
| 6,010,511 A | 1/2000 | Murphy |
| 6,013,679 A | 1/2000 | Kuo |
| 6,024,340 A | 2/2000 | Lazarus |
| 6,024,704 A | 2/2000 | Meador |
| 6,042,345 A | 3/2000 | Bishop |
| 6,048,309 A | 4/2000 | Flom |
| 6,067,991 A | 5/2000 | Forsell |
| 6,074,341 A | 6/2000 | Anderson |
| 6,074,378 A | 6/2000 | Mouri |
| 6,083,249 A | 7/2000 | Familoni |

(56) References Cited

U.S. PATENT DOCUMENTS

| | | | |
|---|---|---|---|
| 6,090,064 | A | 7/2000 | Reilly |
| 6,090,131 | A | 7/2000 | Daley |
| 6,102,678 | A | 8/2000 | Peclat |
| 6,102,922 | A | 8/2000 | Jakobsson |
| 6,117,086 | A | 9/2000 | Shulze |
| 6,129,668 | A | 10/2000 | Haynor |
| 6,164,933 | A | 12/2000 | Tani |
| 6,171,321 | B1 | 1/2001 | Gifford |
| 6,179,569 | B1 | 1/2001 | Kojima |
| 6,193,734 | B1 | 2/2001 | Bolduc |
| 6,203,523 | B1 | 3/2001 | Haller |
| 6,210,345 | B1 | 4/2001 | Van Brunt |
| 6,210,347 | B1 | 4/2001 | Forsell |
| 6,221,024 | B1 | 4/2001 | Miesel |
| 6,224,857 | B1 | 5/2001 | Romeo |
| 6,306,088 | B1 | 10/2001 | Krausman |
| 6,306,116 | B1 | 10/2001 | Hancock |
| 6,327,503 | B1 | 12/2001 | Familoni |
| 6,371,942 | B1 | 4/2002 | Schwartz |
| 6,371,965 | B2 | 4/2002 | Gifford |
| 6,372,494 | B1 | 4/2002 | Naughton |
| 6,383,218 | B1 | 5/2002 | Sourdile |
| 6,383,219 | B1 | 5/2002 | Telandro |
| 6,387,105 | B1 | 5/2002 | Gifford |
| 6,402,717 | B1 | 6/2002 | Reilly |
| 6,402,718 | B1 | 6/2002 | Reilly |
| 6,417,750 | B1 | 7/2002 | Sohn |
| 6,418,934 | B1 | 7/2002 | Chin |
| 6,419,696 | B1 | 7/2002 | Ortiz |
| 6,432,040 | B1 | 8/2002 | Meah |
| 6,439,539 | B1 | 8/2002 | Powell |
| 6,443,957 | B1 | 9/2002 | Addis |
| 6,443,965 | B1 | 9/2002 | Gifford |
| 6,450,173 | B1 | 9/2002 | Forsell |
| 6,450,946 | B1 | 9/2002 | Forsell |
| 6,450,987 | B1 | 9/2002 | Kramer |
| 6,451,034 | B1 | 9/2002 | Gifford |
| 6,453,907 | B1 | 9/2002 | Forsell |
| 6,454,699 | B1 | 9/2002 | Forsell |
| 6,454,700 | B1 | 9/2002 | Forsell |
| 6,454,701 | B1 | 9/2002 | Forsell |
| 6,454,785 | B2 | 9/2002 | De Hoyos Garza |
| 6,457,801 | B1 | 10/2002 | Fish |
| 6,460,543 | B1 | 10/2002 | Forsell |
| 6,461,293 | B1 | 10/2002 | Forsell |
| 6,463,935 | B1 | 10/2002 | Forsell |
| 6,464,628 | B1 | 10/2002 | Forsell |
| 6,470,892 | B1 | 10/2002 | Forsell |
| 6,474,584 | B2 | 11/2002 | Ekich |
| 6,475,136 | B1 | 11/2002 | Forsell |
| 6,475,192 | B1 | 11/2002 | Reilly |
| 6,485,496 | B1 | 11/2002 | Suyker |
| 6,491,704 | B2 | 12/2002 | Gifford |
| 6,491,705 | B2 | 12/2002 | Gifford |
| 6,511,490 | B2 | 1/2003 | Robert |
| 6,517,556 | B1 | 2/2003 | Monassevitch |
| 6,527,701 | B1 | 3/2003 | Sayet |
| 6,547,801 | B1 | 4/2003 | Dargent |
| 6,562,008 | B1 | 5/2003 | Reilly |
| 6,565,582 | B2 | 5/2003 | Gifford |
| 6,579,301 | B1 | 6/2003 | Bales |
| 6,601,604 | B1 | 8/2003 | Cooper |
| 6,615,084 | B1 | 9/2003 | Cigaina |
| 6,630,486 | B1 | 10/2003 | Royer |
| 6,632,239 | B2 | 10/2003 | Snyder |
| 6,635,020 | B2 | 10/2003 | Tripp |
| 6,638,258 | B2 | 10/2003 | Schwartz |
| 6,646,628 | B2 | 11/2003 | Shirochi |
| 6,676,674 | B1 | 1/2004 | Dudai |
| 6,681,135 | B1 | 1/2004 | Davis |
| 6,685,668 | B1 | 2/2004 | Cho |
| 6,685,963 | B1 | 2/2004 | Taupin |
| 6,691,047 | B1 | 2/2004 | Fredericks |
| 6,715,731 | B1 | 4/2004 | Post |
| 6,725,726 | B1 | 4/2004 | Adolfs |
| 6,729,600 | B2 | 5/2004 | Mattes |
| 6,733,478 | B2 | 5/2004 | Reilly |
| 6,754,527 | B2 | 6/2004 | Stroebel |
| 6,767,924 | B2 | 7/2004 | Yu |
| 6,778,927 | B2 | 8/2004 | Cha |
| 6,799,698 | B2 | 10/2004 | Ono |
| 6,808,513 | B2 | 10/2004 | Reilly |
| 6,811,136 | B2 | 11/2004 | Eberhardt |
| 6,820,651 | B2 | 11/2004 | Seuret |
| 6,834,201 | B2 | 12/2004 | Gillies |
| 6,871,090 | B1 | 3/2005 | He |
| 6,889,086 | B2 | 5/2005 | Mass |
| 6,916,326 | B2 | 7/2005 | Benchetrit |
| 6,921,819 | B2 | 7/2005 | Piron |
| 6,924,273 | B2 | 8/2005 | Pierce |
| 6,940,467 | B2 | 9/2005 | Fischer |
| 6,966,875 | B1 | 11/2005 | Longobardi |
| 7,017,583 | B2 | 3/2006 | Forsell |
| 7,017,883 | B2 | 3/2006 | Bayer |
| 7,021,147 | B1 | 4/2006 | Subramanian |
| 7,027,935 | B2 | 4/2006 | Shimase |
| 7,037,344 | B2 | 5/2006 | Kagan |
| 7,040,349 | B2 | 5/2006 | Moler |
| 7,044,933 | B2 | 5/2006 | VanDiver |
| 7,048,519 | B2 | 5/2006 | Fong |
| 7,054,690 | B2 | 5/2006 | Imran |
| 7,058,434 | B2 | 6/2006 | Wang |
| 7,060,080 | B2 | 6/2006 | Bachmann |
| 7,066,486 | B2 | 6/2006 | Lee |
| 7,118,526 | B2 | 10/2006 | Egle |
| 7,119,062 | B1 | 10/2006 | Alvis |
| 7,128,750 | B1 | 10/2006 | Stergiopulos |
| 7,144,400 | B2 | 12/2006 | Byrum |
| 7,172,607 | B2 | 2/2007 | Hoefle |
| 7,177,693 | B2 | 2/2007 | Starkebaum |
| 7,191,007 | B2 | 3/2007 | Desai |
| 7,195,610 | B1 | 3/2007 | Flachbart |
| 7,198,250 | B2 | 4/2007 | East |
| 7,204,821 | B1 | 4/2007 | Clare |
| 7,206,637 | B2 | 4/2007 | Salo |
| 7,223,239 | B2 | 5/2007 | Schulze |
| 7,238,191 | B2 | 7/2007 | Bachmann |
| 7,240,607 | B2 | 7/2007 | Fish |
| 7,255,675 | B2 | 8/2007 | Gertner |
| 7,263,405 | B2 | 8/2007 | Boveja |
| 7,282,023 | B2 | 10/2007 | Frering |
| 7,284,966 | B2 | 10/2007 | Xu |
| 7,288,064 | B2 | 10/2007 | Boustani |
| 7,297,103 | B2 | 11/2007 | Jarsaillon |
| 7,299,082 | B2 | 11/2007 | Feldman |
| 7,310,557 | B2 | 12/2007 | Maschino |
| 7,311,503 | B2 | 12/2007 | Van Lintel et al. |
| 7,311,716 | B2 | 12/2007 | Byrum |
| 7,311,717 | B2 | 12/2007 | Egle |
| 7,314,443 | B2 | 1/2008 | Jordan |
| 7,314,598 | B2 | 1/2008 | Nishino |
| 7,314,636 | B2 | 1/2008 | Caseres |
| 7,338,433 | B2 | 3/2008 | Coe |
| 7,340,306 | B2 | 3/2008 | Barrett |
| 7,351,198 | B2 | 4/2008 | Byrum |
| 7,351,240 | B2 | 4/2008 | Hassler |
| 7,353,747 | B2 | 4/2008 | Swayze |
| 7,364,542 | B2 | 4/2008 | Jambor |
| 7,366,571 | B2 | 4/2008 | Armstrong |
| 7,367,340 | B2 | 5/2008 | Nelson |
| 7,367,937 | B2 | 5/2008 | Jambor |
| 7,374,565 | B2 | 5/2008 | Hassler |
| 7,390,294 | B2 | 6/2008 | Hassler |
| 7,396,353 | B2 | 7/2008 | Lorenzen |
| 7,416,528 | B2 | 8/2008 | Crawford |
| 7,457,668 | B2 | 11/2008 | Cancel |
| 7,481,763 | B2 | 1/2009 | Hassler |
| 7,500,944 | B2 | 3/2009 | Byrum |
| 7,502,649 | B2 | 3/2009 | Ben-Haim |
| 7,507,221 | B2 | 3/2009 | Neer |
| 7,530,943 | B2 | 5/2009 | Lechner |
| 7,585,280 | B2 | 9/2009 | Wilson |
| 7,594,885 | B2 | 9/2009 | Byrum |
| 7,599,743 | B2 | 10/2009 | Hassler |

(56) References Cited

U.S. PATENT DOCUMENTS

| | | |
|---|---|---|
| 7,599,744 B2 | 10/2009 | Giordano |
| 7,601,162 B2 | 10/2009 | Hassler |
| 7,615,001 B2 | 11/2009 | Jambor |
| 7,618,365 B2 | 11/2009 | Jambor |
| 7,658,196 B2 | 2/2010 | Ferreri |
| 7,670,279 B2 | 3/2010 | Gertner |
| 7,699,770 B2 | 4/2010 | Hassler |
| 7,712,470 B2 | 5/2010 | Gertner |
| 7,727,141 B2 | 6/2010 | Hassler |
| 7,741,476 B2 | 6/2010 | Lebreton |
| 7,758,493 B2 | 7/2010 | Gingras |
| 7,763,039 B2 | 7/2010 | Ortiz |
| 7,766,815 B2 | 8/2010 | Ortiz |
| 7,771,439 B2 | 8/2010 | Griffiths |
| 7,775,215 B2 | 8/2010 | Hassler |
| 7,775,966 B2 | 8/2010 | Dlugos |
| 7,775,967 B2 | 8/2010 | Gertner |
| 7,794,386 B2 | 9/2010 | Brooks |
| 7,811,298 B2 | 10/2010 | Birk |
| 7,824,422 B2 | 11/2010 | Benchetrit |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos |
| 7,862,502 B2 | 1/2011 | Pool |
| 7,879,068 B2 | 2/2011 | Dlugos |
| 7,927,270 B2 | 4/2011 | Dlugos |
| 7,951,067 B2 | 5/2011 | Byrum |
| 2001/0011543 A1 | 8/2001 | Forsell |
| 2002/0038105 A1 | 3/2002 | Schwartz |
| 2002/0072780 A1 | 6/2002 | Foley |
| 2002/0091395 A1 | 7/2002 | Gabbay |
| 2002/0095181 A1 | 7/2002 | Beyar |
| 2002/0098097 A1 | 7/2002 | Singh |
| 2002/0123716 A1 | 9/2002 | VanDiver |
| 2002/0133081 A1 | 9/2002 | Ackerman |
| 2002/0139208 A1 | 10/2002 | Yatskov |
| 2002/0152816 A1 | 10/2002 | Kim |
| 2002/0177811 A1 | 11/2002 | Reilly |
| 2002/0183765 A1 | 12/2002 | Adams |
| 2002/0193679 A1 | 12/2002 | Malave |
| 2002/0198548 A1 | 12/2002 | Robert |
| 2003/0009123 A1 | 1/2003 | Brugger |
| 2003/0014003 A1 | 1/2003 | Gertner |
| 2003/0019498 A1 | 1/2003 | Forsell |
| 2003/0045775 A1 | 3/2003 | Forsell |
| 2003/0045902 A1 | 3/2003 | Weadock |
| 2003/0055311 A1 | 3/2003 | Neukermans |
| 2003/0060754 A1 | 3/2003 | Reilly |
| 2003/0060873 A1 | 3/2003 | Gertner |
| 2003/0066536 A1 | 4/2003 | Forsell |
| 2003/0073880 A1 | 4/2003 | Polsky |
| 2003/0093157 A1 | 5/2003 | Casares |
| 2003/0100910 A1 | 5/2003 | Gifford |
| 2003/0120288 A1 | 6/2003 | Benchetrit |
| 2003/0148995 A1 | 8/2003 | Piron |
| 2003/0158564 A1 | 8/2003 | Benchetrit |
| 2003/0158569 A1 | 8/2003 | Wazne |
| 2003/0167022 A1 | 9/2003 | Dijkman |
| 2003/0171887 A1 | 9/2003 | Cha |
| 2003/0181890 A1 | 9/2003 | Schulze |
| 2003/0181917 A1 | 9/2003 | Gertner |
| 2003/0191433 A1 | 10/2003 | Prentiss |
| 2003/0208212 A1 | 11/2003 | Cigaina |
| 2003/0213285 A1 | 11/2003 | Wheeler |
| 2004/0000843 A1 | 1/2004 | East |
| 2004/0034479 A1 | 2/2004 | Shimase |
| 2004/0044332 A1 | 3/2004 | Stergiopulos |
| 2004/0049209 A1 | 3/2004 | Benchetrit |
| 2004/0059393 A1 | 3/2004 | Policker |
| 2004/0068847 A1 | 4/2004 | Belisle |
| 2004/0069714 A1 | 4/2004 | Ferguson |
| 2004/0106899 A1 | 6/2004 | McMichael |
| 2004/0133219 A1 | 7/2004 | Forsell |
| 2004/0147816 A1 | 7/2004 | Policker |
| 2004/0148034 A1 | 7/2004 | Kagan |
| 2004/0153106 A1 | 8/2004 | Dudai |
| 2004/0162595 A1 | 8/2004 | Foley |
| 2004/0171942 A1 | 9/2004 | Ackerman |
| 2004/0215159 A1 | 10/2004 | Forsell |
| 2004/0230137 A1 | 11/2004 | Mouton |
| 2004/0235025 A1 | 11/2004 | Mori |
| 2004/0243057 A1 | 12/2004 | Vinten-Johansen |
| 2004/0254533 A1 | 12/2004 | Schriver |
| 2004/0254536 A1 | 12/2004 | Conlon |
| 2004/0254537 A1 | 12/2004 | Conlon |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0002984 A1 | 1/2005 | Byrum |
| 2005/0038484 A1 | 2/2005 | Knudson |
| 2005/0038498 A1 | 2/2005 | Dubrow |
| 2005/0055039 A1 | 3/2005 | Burnett |
| 2005/0070934 A1 | 3/2005 | Tanaka |
| 2005/0070937 A1 | 3/2005 | Jambor |
| 2005/0082793 A1 | 4/2005 | Lee |
| 2005/0100779 A1 | 5/2005 | Gertner |
| 2005/0104457 A1 | 5/2005 | Jordan |
| 2005/0109973 A1* | 5/2005 | Glime et al. ............... 251/331 |
| 2005/0119672 A1 | 6/2005 | Benchetrit |
| 2005/0119674 A1 | 6/2005 | Gingras |
| 2005/0131383 A1 | 6/2005 | Chen |
| 2005/0131485 A1 | 6/2005 | Knudson |
| 2005/0136122 A1 | 6/2005 | Sadozai |
| 2005/0142152 A1 | 6/2005 | Leshchiner |
| 2005/0143765 A1 | 6/2005 | Bachmann |
| 2005/0143766 A1 | 6/2005 | Bachmann |
| 2005/0154274 A1 | 7/2005 | Jarsaillon |
| 2005/0171568 A1 | 8/2005 | Duffy |
| 2005/0177111 A1 | 8/2005 | Ozeri |
| 2005/0183730 A1 | 8/2005 | Byrum |
| 2005/0192531 A1 | 9/2005 | Birk |
| 2005/0192601 A1 | 9/2005 | Demarais |
| 2005/0192614 A1 | 9/2005 | Binmoeller |
| 2005/0192629 A1 | 9/2005 | Saadat |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan |
| 2005/0244288 A1 | 11/2005 | Oneill |
| 2005/0250979 A1 | 11/2005 | Coe |
| 2005/0251181 A1 | 11/2005 | Bachmann |
| 2005/0251182 A1 | 11/2005 | Bachmann |
| 2005/0267406 A1 | 12/2005 | Hassler |
| 2005/0267500 A1 | 12/2005 | Hassler |
| 2005/0267533 A1 | 12/2005 | Gertner |
| 2005/0271729 A1 | 12/2005 | Wang |
| 2005/0277899 A1 | 12/2005 | Conlon |
| 2005/0283041 A1 | 12/2005 | Egle |
| 2005/0288739 A1 | 12/2005 | Hassler |
| 2005/0288740 A1 | 12/2005 | Hassler |
| 2006/0009697 A1 | 1/2006 | Banet |
| 2006/0015138 A1 | 1/2006 | Gertner |
| 2006/0020298 A1 | 1/2006 | Camilleri |
| 2006/0041183 A1 | 2/2006 | Massen |
| 2006/0074439 A1 | 4/2006 | Garner |
| 2006/0074473 A1 | 4/2006 | Gertner |
| 2006/0079766 A1 | 4/2006 | Neer |
| 2006/0079767 A1 | 4/2006 | Gibbs |
| 2006/0089571 A1 | 4/2006 | Gertner |
| 2006/0122147 A1 | 6/2006 | Wohlrab |
| 2006/0142700 A1 | 6/2006 | Sobelman |
| 2006/0142790 A1 | 6/2006 | Gertner |
| 2006/0149161 A1 | 7/2006 | Wilson |
| 2006/0161139 A1 | 7/2006 | Levine |
| 2006/0161186 A1 | 7/2006 | Hassler |
| 2006/0167531 A1 | 7/2006 | Gertner |
| 2006/0173238 A1 | 8/2006 | Starkebaum |

(56) References Cited

U.S. PATENT DOCUMENTS

| | | |
|---|---|---|
| 2006/0173424 A1 | 8/2006 | Conlon |
| 2006/0178555 A1 | 8/2006 | Bortolotti |
| 2006/0183967 A1 | 8/2006 | Lechner |
| 2006/0189887 A1 | 8/2006 | Hassler |
| 2006/0189888 A1 | 8/2006 | Hassler |
| 2006/0189889 A1 | 8/2006 | Gertner |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212051 A1 | 9/2006 | Snyder |
| 2006/0212053 A1 | 9/2006 | Gertner |
| 2006/0235448 A1 | 10/2006 | Roslin |
| 2006/0246137 A1 | 11/2006 | Hermitte |
| 2006/0247721 A1 | 11/2006 | Maschino |
| 2006/0247722 A1 | 11/2006 | Maschino |
| 2006/0247724 A1 | 11/2006 | Gerber |
| 2006/0252982 A1 | 11/2006 | Hassler |
| 2006/0252983 A1 | 11/2006 | Lembo |
| 2006/0257488 A1 | 11/2006 | Hubbard |
| 2006/0264699 A1 | 11/2006 | Gertner |
| 2006/0264762 A1 | 11/2006 | Starr |
| 2006/0276812 A1 | 12/2006 | Hill |
| 2006/0293627 A1 | 12/2006 | Byrum |
| 2007/0001447 A1 | 1/2007 | Fennington |
| 2007/0015954 A1 | 1/2007 | Dlugos |
| 2007/0015955 A1 | 1/2007 | Tsonton |
| 2007/0015956 A1 | 1/2007 | Crawford |
| 2007/0016231 A1 | 1/2007 | Jambor |
| 2007/0016262 A1 | 1/2007 | Gross |
| 2007/0027356 A1 | 2/2007 | Ortiz |
| 2007/0027358 A1 | 2/2007 | Gertner |
| 2007/0044655 A1 | 3/2007 | Fish |
| 2007/0077292 A1 | 4/2007 | Pinsky |
| 2007/0078476 A1 | 4/2007 | Hull |
| 2007/0106153 A1 | 5/2007 | Neer |
| 2007/0125826 A1 | 6/2007 | Shelton |
| 2007/0156013 A1 | 7/2007 | Birk |
| 2007/0167672 A1 | 7/2007 | Dlugos |
| 2007/0167982 A1 | 7/2007 | Gertner |
| 2007/0173685 A1 | 7/2007 | Jambor |
| 2007/0173888 A1 | 7/2007 | Gertner |
| 2007/0179335 A1 | 8/2007 | Gertner |
| 2007/0185373 A1 | 8/2007 | Tsonton |
| 2007/0185462 A1 | 8/2007 | Byrum |
| 2007/0191717 A1 | 8/2007 | Rosen |
| 2007/0213836 A1 | 9/2007 | Paganon |
| 2007/0218083 A1 | 9/2007 | Brooks |
| 2007/0219597 A1* | 9/2007 | Kamen et al. .................. 607/60 |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann |
| 2007/0250086 A1 | 10/2007 | Wiley |
| 2007/0255335 A1 | 11/2007 | Herbert |
| 2007/0255336 A1 | 11/2007 | Herbert |
| 2007/0265598 A1 | 11/2007 | Karasik |
| 2007/0265645 A1 | 11/2007 | Birk |
| 2007/0265646 A1 | 11/2007 | McCoy |
| 2007/0293716 A1 | 12/2007 | Baker |
| 2007/0298005 A1 | 12/2007 | Thibault |
| 2008/0009680 A1 | 1/2008 | Hassler |
| 2008/0015406 A1 | 1/2008 | Dlugos |
| 2008/0015501 A1 | 1/2008 | Gertner |
| 2008/0027269 A1 | 1/2008 | Gertner |
| 2008/0027469 A1 | 1/2008 | Bachmann |
| 2008/0071306 A1 | 3/2008 | Gertner |
| 2008/0097496 A1 | 4/2008 | Chang |
| 2008/0108862 A1 | 5/2008 | Jordan |
| 2008/0108896 A1 | 5/2008 | Gibbs |
| 2008/0108941 A1 | 5/2008 | Neer |
| 2008/0108943 A1 | 5/2008 | Wagner |
| 2008/0114302 A1 | 5/2008 | Neer |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek |
| 2008/0167647 A1 | 7/2008 | Gertner |
| 2008/0167648 A1 | 7/2008 | Gertner |
| 2008/0172072 A1 | 7/2008 | Pool |
| 2008/0188766 A1 | 8/2008 | Gertner |
| 2008/0195092 A1 | 8/2008 | Kim |
| 2008/0208240 A1 | 8/2008 | Paz |
| 2008/0221598 A1 | 9/2008 | Dlugos |
| 2008/0243071 A1 | 10/2008 | Quijano |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0287969 A1 | 11/2008 | Tsonton |
| 2008/0287974 A1 | 11/2008 | Widenhouse |
| 2008/0287976 A1 | 11/2008 | Weaner |
| 2008/0294097 A1 | 11/2008 | Kim |
| 2008/0300618 A1 | 12/2008 | Gertner |
| 2008/0306443 A1 | 12/2008 | Neer |
| 2008/0319435 A1 | 12/2008 | Rioux |
| 2009/0054914 A1 | 2/2009 | Lechner |
| 2009/0062825 A1 | 3/2009 | Pool |
| 2009/0062826 A1 | 3/2009 | Steffen |
| 2009/0082793 A1 | 3/2009 | Birk |
| 2009/0118572 A1 | 5/2009 | Lechner |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0163803 A1 | 6/2009 | Neer |
| 2009/0171375 A1 | 7/2009 | Coe |
| 2009/0171378 A1 | 7/2009 | Coe |
| 2009/0171379 A1 | 7/2009 | Coe |
| 2009/0187202 A1 | 7/2009 | Ortiz |
| 2009/0188494 A1 | 7/2009 | Imai |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0204141 A1 | 8/2009 | Dlugos |
| 2009/0204179 A1 | 8/2009 | Dlugos |
| 2009/0209995 A1 | 8/2009 | Byrum |
| 2009/0216193 A1 | 8/2009 | Schriver |
| 2009/0216255 A1 | 8/2009 | Coe |
| 2009/0220176 A1 | 9/2009 | Fusco |
| 2009/0222031 A1 | 9/2009 | Axelsson |
| 2009/0222065 A1 | 9/2009 | Dlugos |
| 2009/0228063 A1 | 9/2009 | Dlugos |
| 2009/0228072 A1 | 9/2009 | Coe |
| 2009/0241677 A1 | 10/2009 | Klees |
| 2009/0270759 A1 | 10/2009 | Wilson |
| 2009/0270904 A1 | 10/2009 | Birk |
| 2009/0306462 A1 | 12/2009 | Lechner |
| 2009/0312635 A1 | 12/2009 | Shimchuk |
| 2009/0312785 A1 | 12/2009 | Stone |
| 2010/0010291 A1 | 1/2010 | Birk |
| 2010/0049224 A1 | 2/2010 | Vargas |
| 2010/0087843 A1 | 4/2010 | Bertolote |
| 2010/0099945 A1 | 4/2010 | Birk |
| 2010/0100079 A1 | 4/2010 | Berkcan |

(56) References Cited

U.S. PATENT DOCUMENTS

| | | |
|---|---|---|
| 2010/0145378 A1 | 6/2010 | Gertner |
| 2010/0152532 A1 | 6/2010 | Marcotte |
| 2010/0168508 A1 | 7/2010 | Gertner |
| 2010/0191265 A1 | 7/2010 | Lau |
| 2010/0191271 A1 | 7/2010 | Lau |
| 2010/0204647 A1 | 8/2010 | Gertner |
| 2010/0204723 A1 | 8/2010 | Gertner |
| 2010/0217071 A1 | 8/2010 | Ricol |
| 2010/0226988 A1 | 9/2010 | Lebreton |
| 2010/0228080 A1 | 9/2010 | Tavori |
| 2010/0234682 A1 | 9/2010 | Gertner |
| 2010/0249803 A1 | 9/2010 | Griffiths |
| 2010/0280310 A1 | 11/2010 | Raven |
| 2010/0305397 A1 | 12/2010 | Birk |
| 2010/0312046 A1 | 12/2010 | Lau |
| 2010/0312147 A1 | 12/2010 | Gertner |
| 2010/0324358 A1 | 12/2010 | Birk |
| 2010/0324359 A1 | 12/2010 | Birk |
| 2011/0130626 A1 | 6/2011 | Hassler |
| 2011/0201874 A1 | 8/2011 | Birk |
| 2013/0253262 A1 | 9/2013 | Birk |

FOREIGN PATENT DOCUMENTS

| | | |
|---|---|---|
| CN | 1367670 A | 9/2002 |
| DE | 4225524 | 2/1994 |
| DE | 19802615 A1 | 8/1999 |
| DE | 10020688 | 12/2000 |
| EP | 0119596 | 9/1984 |
| EP | 0230747 | 8/1987 |
| EP | 0416250 | 3/1991 |
| EP | 0611561 | 8/1994 |
| EP | 0695558 | 2/1996 |
| EP | 0876808 | 11/1998 |
| EP | 1036545 A2 | 9/2000 |
| EP | 1072282 | 1/2001 |
| EP | 1105073 | 6/2001 |
| EP | 1396242 A1 | 3/2004 |
| EP | 1396243 A1 | 3/2004 |
| EP | 1491167 | 12/2004 |
| EP | 1491168 | 12/2004 |
| EP | 1529502 | 5/2005 |
| EP | 1547549 A2 | 6/2005 |
| EP | 1574189 | 9/2005 |
| EP | 1600183 A1 | 11/2005 |
| EP | 1602346 A1 | 12/2005 |
| EP | 1704833 A2 | 9/2006 |
| EP | 1719480 A2 | 11/2006 |
| EP | 1754890 | 11/2006 |
| EP | 1736123 A1 | 12/2006 |
| EP | 1736195 | 12/2006 |
| EP | 1736202 | 12/2006 |
| EP | 1743605 A1 | 1/2007 |
| EP | 1829504 | 9/2007 |
| EP | 1829505 | 9/2007 |
| EP | 1829506 | 9/2007 |
| EP | 1949875 | 7/2008 |
| EP | 1967168 A2 | 9/2008 |
| EP | 1922316 | 11/2008 |
| EP | 1992315 | 11/2008 |
| EP | 1992316 A2 | 11/2008 |
| EP | 2074970 A1 | 7/2009 |
| EP | 2074971 A1 | 7/2009 |
| EP | 2074972 A2 | 7/2009 |
| EP | 2087862 A1 | 8/2009 |
| EP | 2095796 A1 | 9/2009 |
| EP | 2095797 A2 | 9/2009 |
| EP | 2095798 | 9/2009 |
| EP | 2191796 | 6/2010 |
| FR | 1566202 | 5/1969 |
| FR | 2688693 | 9/1993 |
| FR | 2769491 | 4/1999 |
| FR | 2783153 | 3/2000 |
| FR | 2797181 A1 | 2/2001 |
| FR | 2799118 | 4/2001 |
| FR | 2823663 A1 | 10/2002 |
| FR | 2855744 A1 | 12/2004 |
| FR | 2921822 A1 | 4/2009 |
| GB | 1174814 A | 12/1969 |
| GB | 2090747 | 7/1982 |
| JP | 57171676 | 10/1982 |
| JP | 167309 | 4/1989 |
| JP | 2019147 | 1/1990 |
| JP | 2132104 | 11/1990 |
| JP | 3105702 | 11/1991 |
| JP | 11244395 | 9/1999 |
| JP | 2003526410 | 9/2003 |
| JP | 2005131380 | 5/2005 |
| JP | 2005334658 | 12/2005 |
| SE | 8503144 | 12/1986 |
| WO | 8600079 | 1/1986 |
| WO | 8600912 | 2/1986 |
| WO | 8911701 | 11/1989 |
| WO | 9000369 | 1/1990 |
| WO | 9220349 | 11/1992 |
| WO | 9402517 | 2/1994 |
| WO | 9633751 | 1/1996 |
| WO | 9835639 | 8/1998 |
| WO | 9835640 | 8/1998 |
| WO | 0000108 A1 | 1/2000 |
| WO | 0001428 | 1/2000 |
| WO | 0009047 A1 | 2/2000 |
| WO | 0009048 A1 | 2/2000 |
| WO | 0009049 | 2/2000 |
| WO | 0015158 A1 | 3/2000 |
| WO | 0066196 | 11/2000 |
| WO | 0110359 | 2/2001 |
| WO | 0112078 | 2/2001 |
| WO | 0141671 | 6/2001 |
| WO | 0147435 | 7/2001 |
| WO | 0147575 | 7/2001 |
| WO | 0149245 | 7/2001 |
| WO | 0152777 | 7/2001 |
| WO | 0168007 | 9/2001 |
| WO | 0170131 | 9/2001 |
| WO | 0185071 | 11/2001 |
| WO | 0205753 | 1/2002 |
| WO | 0209792 | 2/2002 |
| WO | 0219953 | 3/2002 |
| WO | 0226317 | 4/2002 |
| WO | 02053093 | 7/2002 |
| WO | 02065948 | 8/2002 |
| WO | 02096326 | 12/2002 |
| WO | 03007782 | 1/2003 |
| WO | 03055420 | 7/2003 |
| WO | 03057092 | 7/2003 |
| WO | 03059215 | 7/2003 |
| WO | 03077191 | 9/2003 |
| WO | 03101352 A1 | 12/2003 |
| WO | 03105732 A1 | 12/2003 |
| WO | 2004014245 A1 | 2/2004 |
| WO | 2004019671 A2 | 3/2004 |
| WO | 2004108025 | 12/2004 |
| WO | 2004112563 A2 | 12/2004 |
| WO | 2005007232 | 1/2005 |
| WO | 2005009305 A1 | 2/2005 |
| WO | 2005067994 | 7/2005 |
| WO | 2005072195 | 8/2005 |
| WO | 2005087147 | 9/2005 |
| WO | 2005094447 | 10/2005 |
| WO | 2005112888 | 12/2005 |
| WO | 2006040647 | 4/2006 |
| WO | 2006049725 | 5/2006 |
| WO | 2006083885 | 8/2006 |
| WO | 2006108203 A2 | 10/2006 |
| WO | 2007067206 | 6/2007 |
| WO | 2007081304 A2 | 7/2007 |
| WO | 2007106727 A2 | 9/2007 |
| WO | 2007114905 | 10/2007 |
| WO | 2007145638 | 12/2007 |
| WO | 2008063673 A1 | 5/2008 |
| WO | 2008109300 A2 | 9/2008 |
| WO | 2008134755 | 11/2008 |

(56) References Cited

FOREIGN PATENT DOCUMENTS

| WO | 2009023247 | | 2/2009 |
|---|---|---|---|
| WO | 2009050709 | A2 | 4/2009 |
| WO | 2009132127 | A1 | 10/2009 |
| WO | 2009136126 | A2 | 11/2009 |
| WO | 2010042493 | A1 | 4/2010 |

OTHER PUBLICATIONS

Acuna-Goycolea et al.; 'Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus'; The Journal of Neuroscience; V. 25(32); pp. 7406-7419; Aug. 10, 2005.

Adrian et al.; 'Mechanism of Pancreatic Polypeptide Release in Man.' The Lancet; pp. 161-163; Jan. 22, 1977.

Anson; 'Shape Memory Alloys—Medical Applications,' Source: Materials World, vol. 7, No. 12, pp. 745-747, Dec. 1999.

Asakawa et al; 'Antagonism of Ghrelin Receptor Reduces Food Intake and Body Weight Gain in Mice'; Gut.; V.52; pp. 947-952; 2003.

Baggio et al. 'Biology of Integrins: GLP-1 and GIP'; Gastroenrology; V. 132; pp. 2131-2157; 2007.

Ballantyne; 'Peptide YY(1-36) and Peptide YY(3-36): Part I. Distribution, Release, and Actions'; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; 'Physiology'; V. 5; pp. 55-57, 210, 428, 540, 554, 579, 584, 591; 2004.

BioEnterics Corporation, an Inamed Company, BioEnterics Intragastric Balloon; Directions for Use Published Document, P/N 94200 Rev: B, pp. 1-56.

Bio Enterics Lap-Band Adjustable Gastric Banding System, Inamed Health, pub. Aug. 28, 2003, pp. 1-115.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Burdyga et al.; 'Cholecystokinin Regulates Expression of Y2 Receptors in Vagal Afferent Neurons Serving the Stomach'; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Corno et al.; 'A new implantable device for telemetric control of pulmonary blood flow'; New ideas; received Apr. 24, 2004; received in revised form Jul. 12, 2002; 10 pages.

Corno et al.; 'FlowWatchTM in clipped and inclipped position'; Interact Cardio Vase Thorac Surg 2002; 1:46-49; Copyright@2002 The European Asociation for Cardio-thoracic Surgery; 1 page.

Cummings et al.; 'Plasma Ghrelin Levels After Diet-Induced Weight Loss or Gastric Bypass Surgery'; N. Engl J. Med; V. 346, No. 21; pp. 1623-1630; May 23, 2002.

Cummings; 'Gastrointestinal Regulation of Foot Intake'; The Food Journal of Clinical Investigation; V. 117, N. 1; pp. 13-23; Jan. 2007.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

De Waele et al.; "Endoscopic Volume Adjustment of Intragastric Balloons for Intolerance"; Obesity Surgery; V. 11; pp. 223-224; 2001.

De Waele et al.; "Intragastric Balloons for Preoperative Weight Reduction"; Obesity Surgery; V. 58; pp. 58-60; 2001.

Desai et al.; 'Molecular Weight of Heparin Using 13C Nuclear Magnetic Resonance Spectroscopy' Journal of Pharmaceutical Science, V. 84,12; 1995, Abstract only.

Doldi et al.; 'Intragastric Balloon: Another Option for Treatment of Obesity and Morbid Obesity'; Hepato-Gastroenterology; V. 51, N. 55; pp. 294-307; Jan.-Feb. 2004.

Doldi et al.; 'Treatment of Morbid Obesity with Intragastric Balloon in Association with Diet'; Obesity Surgery; V. 10, pp. 583-587; 2000.

Ekblad et al.; 'Distribution of Pancreatic Peptide and Peptide-YY'; Peptides; V. 23; pp. 251-261;2002.

El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.

Galloro et al; "Preliminary Endoscopic Technical Report of an New Silicone Intragastric Balloon in the Treatment of Morbid Obesity"; Obesity Surgery; V. 9, pp. 68-71; 1999.

GinShiCel MH Hydroxy Propyl Methyl Cellulose, Web Page http://www.ginshicel.cn/MHPC.html, Nov. 12, 2008.

Girard; 'The Incretins: From the concept to their use in the treatment of type 2 diabetes. Part A: IncretinsIncretinsIncretinsIncretinsIncretins: Concept and physiological functions'; Diabetes and Metabolism; V. 34; pp. 550-559; 2008.

Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.

Grise et al.; "Peptide YY Inhibits Growth of Human Breast Cancer in Vitro and in Vivo"; Journal of Surgical Research; V. 82; pp. 151-155; 1999.

Grundy; "Signaling the State of the Digestive Tract"; Autonomic Neuroscience: Basic and Clinical; V. 125; pp. 76-80; 2006.

Grundy; "Vagal Control of Gastrointestinal Function"; Bailliere's Clinical Gastroenterology; V. 2; No. 1; pp. 23-43; 1988.

Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.

Hameed et al., 'Gut Hormones and Appetite Control', Oral Diseases, 2009, 15:18-26.

Hassan et al.; 'Effects of Adjuvants to Local Anesthetics on Their Duration III Experimental Studies of Hyaluronic Acid' Abstract Pub Med [Acta Anesthesiol Scand.; 29 (4): 384-8], 1 page; May 1985.

Hodson et al.; 'Management of Obesity with the New Intragastric Balloon'; Obesity Surgery; V. 11, pp. 327-329,2001.

Holzer; "Gastrointestinal Afferents as Targets of Novel Drugs for the Treatment of Functional Bowel Disorders and Visceral Pain"; European Journal of Pharmacology; V. 429; pp. 177-193; 2001.

Houpt; 'Gastrointestinal Factors in Hunger and Satiety'; Neurosci. and Behav. Rev.; V. 6; pp. 145-164; 1982.

Iverson et al.; 'Recent Advances in Microscale Pumping Technologies: A Review and Evaluation'; Microfluid Nanofluid; vol. 5; pp. 145-174; Feb. 19, 2008.

Jones; "Molecular, pharmacological, and clinical aspects of liraglutide, a oncedaily human GLP-1 analogue"; Molecular and Cellular Endocrinology; V. 297; pp. 137-140; 2009.

Kerem et al.; 'Exogenous Ghrelin Enhances Endocrine and Exocrine Regeneration in Pancreatectomized Rats'; J. Gastrointest Surg.; V. 13; pp. 775-783, 2009.

Kesty et al., 'Hormone-based Therapies in the Regulation of Fuel Metabolism and Body Weight', Expert Opin. Biol. Ther., 2008, 8(11): 1733-1747.

(56) References Cited

OTHER PUBLICATIONS

Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Kojima et al., 'A Role for Pancreatic Polypeptide in Feeding and Body Weight Regulation', Peptides, 2007, 28:459-463.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; 'Gut Hormone Profiles Following Bariatric Surgery Favor an Anorectic State, Facilitate Weight Loss, and Improve Metabolic Parameters'; Ann. Surg; V. 243; No. 1; pp. 108-114; Jan. 2006.
Liu et al.; 'Adjuvant Hormonal Treatment With Peptide YY or Its Analog Decreases Human Pancreatic Carcinoma Growth'; The American Journal of Surgery; V. 171; pp. 192-196; Jan. 1996.
Mathus-Vliegen et al. 'Intragastric Balloons for Morbid Obesity: Results, Patient Tolerance and Balloon Life Span'; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; 'Processing and metabolism of Peptide-YY: Pivotal roles of Dipeptidase-IV, Aminopeptidase-P, and Endopeptidase-24. 11'; Endocrinology; V. 134, No. 5; pp. 2088-2094;1994.
Naslund et al.; 'Prandial Subcutaneous Injection of Glucagon-Like Peptide'; Br. J. Nutr.; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; 'Pulmonary delivery of a GLP-1 receptor agonist, BMS-686117'; International Journal of Pharmaceutics; V. 366; pp. 218-220; 2008.
Rang et al.; 'Pharmacology'; V. 5; pp. 203, 397, 402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. 'Peptide YY: A Potential Therapy for Obesity'; Current Drug Targets; V. 6; pp. 171-179; 2005.
Sannino et al., 'Crosslinking of Cellulose Derivatives and Hyaluronic Acid with Water-Soluble Carbodiimide,' Polymer 46(2005)pp. 11206-11212.
Shechter et al.; "Reversible PEGylation of peptide YY3-36 prolongs its inhibition of food intake in mice"; FEBS Letters; V. 579; pp. 2439-2444; 2005.
Silver et al.; 'Physical Properties of Hyaluronic Acid and Hydroxypropylmethylcellulose in Solution: Evaluation of Coating Ability' Journal of Applied Biomaterials, V. 5; pp. 89-98, 1994.
Small et al.; 'Gut hormones and the control of appetite'; Trends in Endocrinology and Metabolism; V. 15; No. 6; pp. 259-263; Aug. 2004.
Stanley et al.; 'Gastrointestinal Satiety Signals III. Glucagon-like Peptide 1, oxyntomodulin, peptide YY, and pancreatic polypeptide'; Am. J. Physiol Gastrointest Liver Physiol; V. 286; pp. 693-697; 2004.
Tezel,'The Science of Hyaluronic Acid Dermal Fillers,' Journal of Cosmetic and Laser Therapy (2008) 10: pp. 35-42.
Tolhurst et al.; 'Nutritional regulation of glucagon-like peptidel secretion'; J. Physiol.; V. 587, No. I;pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; 'Y4 Receptors Mediate the Inhibitory Responses of Pancreatic Polypeptide in Human and Mouse Colon Mucosa'; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wahlen et al.; 'The BioEnterics Intragastric Balloon (BIB): How to Use It'; Obesity Surgery; V. 11; pp. 524-527; 2001.
Wang et al.; "Plasma Ghrelin Modulation in Gastric Band Operation and Sleeve Gastrectomy"; Obes. Surg.; pp. 357-362; 2008.
Weiner et al.; 'Preparation of Extremely Obese Patients for Laparoscopic Gastric Banding by Gastric Balloon Therapy'; Obesity Surgery; V. 9, pp. 261-264, 1999.
Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.
Yuzuriha et al.; "Gastrointestinal Hormones (anorexigenic peptide YY and orexigenic ghrelin) influence neural tube development"; FASEB J.; V. 21; pp. 2108-2112; 2007.
Brown et al; 'Symmetrical Pouch Dilation After Laparoscopic Adjustable Gastric Banding: Incidence and Management'; Obesity Surgery; V. 18, pp. 1104-1108; 2008.
Ceelen et al.; 'Surgical Treatment of Severe Obesity With a Low-Pressure Adjustable Gastric Band: Experimental Data and Clinical Results in 625 Patients'; Annals of Surgery; V. 237, No. I;pp. 10-16; 2003.
Dixon et al.; 'Pregnancy After Lap-Band Surgery: Management of the Band to Achieve Healthy Weight Outcomes'; Obesity Surgery; V. 11, pp. 59-65; 2001.
Helioscopie Product Insert for Heliogast, pp. 1-11 (undated).
Neary et al.; 'Peptide YY(3-36) and Glucagon-Like Peptide-1.sub. (7-36) Inhibit Food Intake Additively'; Endocrinology; V.146; pp. 5120-5127; 2005.
Padidela et al.; 'Elevated basal and post-feed glucagon-like petide 1 (GLP-1) concentrations in the neonatel period'; European Journal of Endocrinology; v. 160; pp. 53-58; 2009.
Patient Management After Lap-Band Placement; http://www.core.monash.org/ patient-care.pdf.
Shi et al; 'Sexually Dimorphic Responses to Fat Loss After Caloric Restriction or Surgical Lipectomy'; Am. J. Physiol. Endocrinol. Metab.; V. 293; E316-E326; 2007.
The Lap-Band Device & How it Works; http://lapband.com/en/learn_about-lapband/device_how_it_works/.
Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

\* cited by examiner

DOME AND SCREW VALVES FOR REMOTELY ADJUSTABLE GASTRIC BANDING SYSTEMS

CROSS REFERENCE TO RELATED APPLICATIONS

This application is a continuation of U.S. patent application Ser. No. 12/712,952, filed Feb. 25, 2010, which is a continuation-in-part of U.S. patent application Ser. No. 12/603,058, filed Oct. 21, 2009, now U.S. Pat. No. 8,366,602, which claims the benefit of U.S. Provisional Patent Application No. 61/107,576, filed Oct. 22, 2008, the entire disclosure of each of these applications are incorporated herein by reference.

FIELD

The present invention generally relates to medical systems and apparatus and uses thereof for treating obesity and/or obesity-related diseases, and more specifically, relates to dome and screw valves for remotely adjustable gastric banding systems.

BACKGROUND

Adjustable gastric banding systems provide an effective and substantially less invasive alternative to gastric bypass surgery and other conventional surgical weight loss procedures. Despite the sustained weight loss of invasive weight loss procedures, such as gastric bypass surgery, it has been recognized that sustained weight loss can also be achieved through a laparoscopically-placed gastric band, for example, the LAP-BAND® (Allergan, Inc., Irvine, Calif.) gastric band or the LAP-BAND APO (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach provides a feeling of satiety or fullness that discourages overeating. Unlike gastric bypass surgery procedures, adjustable gastric banding systems are reversible and require no permanent modification to the gastrointestinal tract.

Over time, a stoma created by the gastric band may need an adjustment in order to maintain an appropriate size, which is neither too restrictive nor too passive. Prior art gastric banding systems provide a subcutaneous fluid access port connected to an expandable or inflatable portion of the gastric band. By adding fluid to or removing fluid from the inflatable portion by means of a hypodermic needle inserted into the fluid access port, the effective size of the gastric band can be adjusted to provide a tighter or looser constriction.

It would be desirable to allow for non-invasive adjustment of gastric band constriction, for example, without the use of the hypodermic needle. Thus, remotely adjustable gastric banding systems capable of non-invasive adjustment are desired and described herein.

SUMMARY

In one example embodiment of the present invention, there is an implantable device that controls the movement of fluid to an inflatable portion of a gastric band. The implantable device includes a body. The body has an inlet, an outlet and a valve seat positioned between the inlet and the outlet. The body defines a fluid passage from the inlet to the outlet.

The implantable device also includes a diaphragm. The diaphragm has one or more edges coupled to the body. The diaphragm is made of an elastomeric material and capable of being moved between a closed position that blocks the valve seat and does not allow the fluid to move from the inlet to the outlet and an open position that does not block the valve seat and allows the fluid to move from the inlet to the outlet.

The implantable device also includes an actuator. The actuator is configured to apply a force on the diaphragm causing the diaphragm to move from the closed position to the open position. The implantable device also includes a microcontroller coupled to the actuator, the microcontroller configured to receive a telemetric signal from a remote transmitter and control the actuator based on the telemetric signal.

In another example embodiment of the present invention, there is an implantable device that controls the movement of fluid to an inflatable portion of a gastric band. The implantable device includes a body. The body has an inlet, an outlet and a valve seat. The body defines a fluid passage from the inlet to the outlet.

The implantable device also includes a valve seal. The valve seal has one or more edges coupled to the body. The valve seal is made of an elastomeric material and is capable of being moved between an open position that does not block the valve seat and allows the fluid to move from the inlet to the outlet and a closed position that blocks the valve seat and does not allow the fluid to move from the inlet to the outlet.

The implantable device also includes an actuator. The actuator is positioned within the body. The actuator has an actuator body defining a threaded screw hole and a screw positioned within the threaded screw hole. The screw is configured to apply a force on the valve seal causing the valve seal to move from the open position to the closed position when the actuator receives a telemetric signal from an implantable microcontroller. A first telemetric signal may be used to move the valve seal from the open position to the closed position and a second telemetric signal may be used to move the valve seal from the closed position to the open position.

DETAILED DESCRIPTION

The present invention generally provides remotely adjustable gastric banding systems, for example, for treatment of obesity and obesity related conditions, as well as systems for controlling inflation of a gastric banding system.

Remotely adjustable gastric banding systems, otherwise referred to as a remotely adjustable band (RAB), include one or more medical devices, or a system, which allows a healthcare worker to adjust a gastric band without requiring a hypodermic needle to be inserted into an implanted access port. The RAB may use a remote transmitter to send radiofrequency signals or telemetric signals for powering and communicating with an implanted device of the RAB. The implanted device can fill or drain a gastric band of the RAB as requested by the healthcare worker via the remote transmitter. In between filling and draining adjustments to the gastric band, the volume of fluid contained in the gastric band ideally remains unchanged.

In one embodiment, a dome valve is used to pass and block fluid. The dome valve has an actuator that can adjust an elastomeric diaphragm (e.g., a valve seal) to an open or closed position. The dome valve can be used safely during magnetic resonance imaging (MRI) since the dome valve does not have a significant amount of ferromagnetic material. The elastomeric diaphragm is also inexpensive and robust.

In another embodiment, a screw valve is used to pass and block fluid. The screw valve has a screw that can adjust a valve seal to multiple precise positions, not just fully open or fully closed. The screw valve can be used in a high pressure environment since no force is required to maintain a position and because the screw can be driven to create a tight seal.

Figure 1:
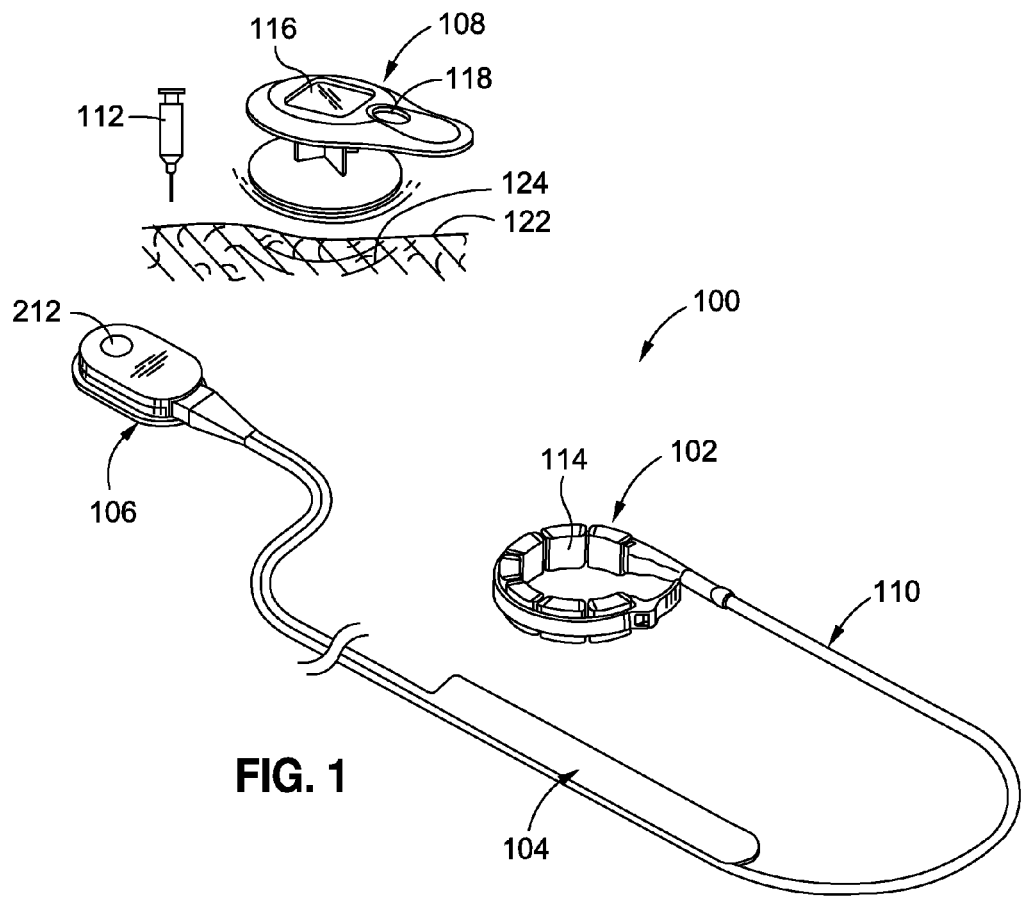
FIG. 1 illustrates a perspective view of a remotely adjustable gastric banding system according to an embodiment of the present invention.

FIG. 1 illustrates a perspective view of a remotely adjustable gastric banding system 100 according to an embodiment of the present invention. The gastric banding system 100 includes a gastric band 102, a reservoir 104, a high precision pump unit 106, a remote transmitter 108 and tubing 110. The skin 122 of a human illustrates a separation between implantable components and non-implantable components. As illustrated, the remote transmitter 108 (e.g., a remote controller unit) is non-implantable, whereas the gastric band 102, the reservoir 104, the high precision pump unit 106, and the tubing 110 are implantable (e.g., an implantable device), and can be implanted in the human using conventional surgical techniques. The high precision pump unit 106 can be used to replace or complement a conventional access port for adjusting inflation or deflation of the gastric band 102. In some embodiments, the system includes an override port 212 which can be used, for example, with a hypodermic needle 112, to fill and drain the gastric band 102.

The high precision pump unit 106 is connected to the reservoir 104 and the gastric band 102 via the tubing 110, and can move precisely metered volumes of fluid (e.g., saline) in or out of the gastric band 102. Moving the fluid into the gastric band 102 causes inflation of at least one bladder, or an inflatable portion 114 (e.g., inflatable member) and constricts around the cardia, or upper portion of the stomach, forming a stoma that restricts the passage of food into a lower portion of the stomach. This stoma can provide a patient with a sensation of satiety or fullness that discourages overeating. In contrast, moving the fluid out of the inflatable portion 114 of the gastric band 102 reduces the pressure around the cardia and allows the stoma to be at least partially released and allows the human to regain a hunger sensation.

The high precision pump unit 106 is implanted within a patient, and therefore, is non-biodegradable. The encasement or housing of the high precision pump unit 106 may be non-hermetically sealed or hermetically sealed from the in situ environment (e.g., undisturbed environment) in the patient and formed at least partially of any rugged plastic material including, polypropylene, cyclicolephin co-polymer, nylon, and other compatible polymers and the like or at least partially formed of a non-radiopaque metal. The housing has a smooth exterior shape, with no jagged edges, to minimize foreign body response and tissue irritation. The high precision pump unit 106 is also sterilizable, in one embodiment, dry heat sterilizable before implantation.

The reservoir 104 may be a soft, collapsible balloon made of a biocompatible polymer material, for example, silicone, which holds a reserve of a biocompatible fluid, for example, saline, to allow for adjustments in the size of the gastric band 102. In one embodiment, the reservoir 104 is fully collapsible and can contain the extra fluid required to increase the volume of the gastric band 102 to therapeutic levels. Further, the reservoir 104 also may have excess capacity so the gastric band 102 may be fully drained into it without the reservoir 104 being filled beyond its maximum capacity.

The reservoir 104 may represent one or both of a source reservoir and a drain reservoir, where the source reservoir provides fluid to the gastric band 102, and the drain reservoir receives fluid from the gastric band 102.

The fluids used within the systems of the present invention may include any fluid that is biocompatible. The fluid has no adverse effect on the patient in the unlikely event that a leak emanates from the system. The fluid can simply be water or any biocompatible polymer oil such as castor oil. In an example embodiment, the fluid is saline.

The tubing 110 is any biocompatible flexible tubing that does not degrade in vivo (e.g., within the human). The tubing 110 is configured to withstand hydraulic pressure up to about 30 psi (about 206 kPa) without leakage. This hydraulic pressure tolerance is true of the entire fluid path of the systems described herein. Although the systems described herein do not generally leak, if they do, fluid is not lost at a rate greater than about 0.2 cc/yr, or about 0.1 cc/yr.

Other biocompatible and biostable polymers which are useful for forming the reservoir 104 and the tubing 110 include:

polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The systems and apparatus described herein further include the remote transmitter 108 (e.g., a remote controller unit), which provides access to system data and functions, and can be an external, handheld, reusable battery-powered device. The remote transmitter 108 can be made of any rugged plastic material including polypropylene, cyclicolephin co-polymer, nylon, and other compatible polymers and the like. The remote transmitter 108 is not implanted within the patient so hermetic sealing of the unit is not required. However, in one embodiment, the remote transmitter 108 is at least water resistant, if not waterproof, and can be cleaned using standard hospital disinfectants without damage to the unit.

Further, the remote transmitter 108 has a user interface including at least one display 116 and at least one user input 118. In some example embodiments, the display 116 and the user input 118 are combined in the form of a touch screen with a color display. In other embodiments, the display is grayscale. The remote transmitter 108 permits a clinician or a medical technician to navigate through menu driven screens used for data entry, data collection, and controlling the high precision pump unit 106.

The remote transmitter 108 is capable of communicating with the high precision pump unit 106. "Capable of communicating" as used herein refers to the remote controller's ability to establish communications with the high precision pump unit 106 yet still have the ability to break communication and the systems described herein still function. To establish communication, in one example embodiment, once the remote transmitter 108 is initialized, the display 116 shows a searching query for a nearby high precision pump unit 106. As the remote transmitter 108 is brought into range of the high precision pump unit 106, a symbol displays the strength of the communication link. Once stable communications have been acquired, the display 116 shows the serial number of the system so a clinician can verify they have the appropriate patient records in hand. If the patient requires a tightening of the gastric band 102, the clinician can enter the amount of the desired volume increase. The remote transmitter 108 can also display the current volume within the gastric band 102 and indicate the new volume as the gastric band 102 fills. The display 116 can also indicate desired and actual volumes during draining of the gastric band 102.

To verify the appropriate adjustment has been made to the system, the clinician can set the remote transmitter 108 into a pressure monitor mode and request that the patient drink water. The display 116 shows a real time graph of the pressure measured within the gastric band 102. This diagnostic tool may show higher pressures and warning messages if the gastric band 102 has been over-tightened.

The remote transmitter 108 can synchronize and charge when coupled with a charging cradle or docking station. This docking station provides the ability to recharge a rechargeable battery of the remote transmitter 108 and provides a link to download information to a personal computer such as the adjustment history of a patient. Other data that can be stored on the remote transmitter 108 and downloaded from the high precision pump unit 106 includes, but is not limited to serial number, gastric band size, patient information, firmware version and patient adjustment history. This data can be downloaded directly to a patient tracking database for easy tracking.

Any data stored on the remote transmitter 108 or within the high precision pump unit 106 can be electronically secured. In other words, security measures can be put in place to keep the data confidential, including communication between the high precision pump unit 106 and the remote transmitter 108. Security measures can include computer generated algorithms that prevent intrusion by outside parties.

The high precision pump unit 106 can contain a microfluidic pump with active valves. In such an embodiment, the high precision pump unit 106 is a passive device that can only be powered by the remote transmitter 108 when it is in close proximity. For example, in one example embodiment, the remote transmitter 108 may be configured to power and communicate with the high precision pump unit 106 at any distance less than about 8 inches, in one embodiment less than about 4 inches (about 10.2 cm) of tissue plus about 4 inches of air, and in another embodiment about 2 inches (about 5.1 cm) of air. Power and communications can be tailored to transmit over longer distances or can be tailored to have the remote transmitter 108 placed on the skin adjacent to the high precision pump unit 106.

Further, the remote transmitter 108 can provide an inductive power and telemetric control through a transmission 124 to the high precision pump unit 106. The remote transmitter 108 may be configured to provide continuous power to the high precision pump unit 106. A dedicated microcontroller within the remote transmitter 108 monitors the amount of power that is transmitted. Further still, a power management system may be implemented to optimize energy transmission between the remote transmitter 108 and the high precision pump unit 106 relative to their separation distance. For example, the power transmission may automatically decrease as the remote transmitter 108 is closer to the high precision pump unit 106, and may be increased as the distance is increased. This minimizes wasted energy, and energy exposure to the patient.

The systems and apparatus described herein use common surgical techniques to place the components in their respective positions within a patient. The surgical techniques may be identical or similar to those used in the placement of conventional gastric banding systems. For example, the gastric band 102 may be placed around the stomach using laparoscopic techniques, as known to those of skill in the art. Like a conventional access port, the high precision pump unit 106 may be sutured onto the rectus muscle sheath or any other conveniently accessible muscle. In order to achieve a secure attachment of the high precision pump unit 106, the unit shall be sutured to the rectus muscle and remain securely attached for forces below about 6 lbf, in one embodiment below about 3 lbf (13.3 N). The tubing 110 from the high precision pump unit 106 passes through the rectus muscle into the peritoneal cavity in the same manner as the tubing of a conventional access port.

The systems and apparatus of the present invention further allow for a remotely controlled adjustment without needles, non-invasively, by using the remote transmitter 108. Also, should the remote transmitter 108 be unavailable, damaged, out of power, or in the event of an emergency, an adjustment of the gastric band 102 can be performed invasively using a needle. By using the override port 212, a clinician can choose to use the hypodermic needle 112, a standard needle, or a syringe for adjustments. If any of the electronics associated with the systems and apparatus described herein become inoperable, the override port 212 can be used to add or remove fluid from the gastric band 102. The override port 212 and the hypodermic needle 112 can always be used to adjust the gastric band 102.

Figure 2:
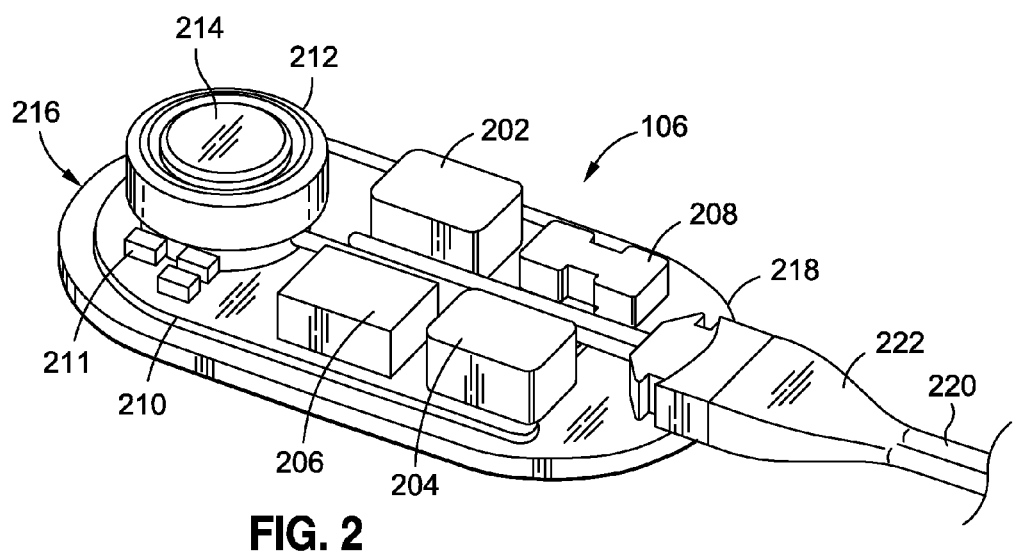
FIG. 2 illustrates an example configuration of the internal components of the high precision pump unit illustrated in FIG. 1 according to an embodiment of the present invention.

FIG. 2 illustrates an example configuration of the internal components of the high precision pump unit 106 illustrated in FIG. 1 according to an embodiment of the present invention. The housing of the high precision pump unit 106 has an internal volume of between about 0.75 in$^3$ to about 1.6 in$^3$. Exemplary internal features of the high precision pump unit 106 that fit within the housing include a first valve 202, a second valve 204, a pump 206, a pressure/flow sensor 208, an electronics board 210 including an antenna 211, and the override port 212. The internal components of the high precision pump unit 106 can be arranged in any fashion appropriate for delivering and removing precise amounts of fluid from the gastric band 102 and the reservoir 104.

The pump 206 can be actively or passively driven. If the pump 206 is actively driven, a local power source such as a battery (not illustrated) is provided to drive the pump 206. If the pump 206 is passively driven, it may be inductively powered by a device external to the high precision pump unit 106. In an exemplary configuration, the pump 206 is passively driven through inductive power from the remote transmitter 108.

In one example embodiment, the pump 206 is an inductively powered, electrically driven, positive displacement piezoelectric pump. The pump 206 provides a means to move fluid into the gastric band 102.

The pump 206 can move fluid from the reservoir 104 to the gastric band 102 at rates higher than about 0.5 cc/min, for example, higher than about 1 cc/min for band pressures less than about 20 psi (about 138 kPa) relative to the reservoir pressure. Alternatively, fluid can be drained from the gastric band 102 to the reservoir 104 at rates higher than about 0.5 cc/min, for example, higher than about 1 cc/min for band pressures above about 0.2 psi (about 1.38 kPa).

The first valve 202 and the second valve 204, illustrated in FIG. 2, can be any valve known in the art to allow precise delivery of fluid and precise flow rates therethrough. In one embodiment, the first valve 202 and the second valve 204 only allow fluid to move in one direction, therefore, the two valves are situated in parallel with the high precision pump unit 106 allowing fluid to drain back from the gastric band 102. Further, the first valve 202 and the second valve 204 should have a precision orifice that restricts the flow rate to a well-characterized, precise amount.

The gastric banding system 100 may further comprise at least one flow or pressure sensor 208 disposed, for example, within or adjacent to the high precision pump unit 106. In an exemplary embodiment, two pressure sensors are situated within the fluid pathway between the first valve 202 and the second valve 204 and the gastric band 102. During a no-flow condition, both of the pressure sensors may be used to measure pressure thereby providing the benefits of redundancy and averaging.

For example, sensing or measuring the pressure within the fluid pathway of the gastric banding system 100 provides diagnostic uses. A clinician can measure pressure while a patient drinks water, recording and analyzing resulting pressure fluctuations which can help determine if the gastric band 102 is too restrictive. Whether the gastric band 102 is too restrictive can also be confirmed by the patient's response (generally discomfort) upon drinking the water, and can then be appropriately adjusted. Further, sensing or measuring pressure in the gastric banding system 100 can be useful in diagnosing system leaks or obstructions. For example, if the pressure consistently drops over an extended period of time, the clinician can diagnose a leak within the system and plan for an appropriate treatment to fix the problem. In contrast, if there is an obstruction within the system with a sustained pressure rise over time, the clinician can diagnose an obstruction within the system and plan for an appropriate treatment to fix the problem.

The override port 212, as illustrated in FIGS. 1 and 2, is an optional feature of some of the embodiments of the present invention. The override port 212 can be manufactured from a metal or a non-radiopaque material and is accessible by insertion of the hypodermic needle 112 (in FIG. 1) through a self-sealing septum 214 (in FIG. 2). The override port 212 allows a clinician to use the hypodermic needle 112 or a standard syringe to fill or drain the gastric band 102. Further, the override port 212 may be located on the distal end 216 of the high precision pump unit 106, for example, at a position substantially opposite from the proximal end 218 where the tubing 220 extends from the high precision pump unit 106. This placement of the override port 212 thereby reduces possible occurrences of a needle damaging the tubing 220. An extension body 222 emanating from the high precision pump unit 106 further protects the tubing 220 from accidental needle sticks.

The high precision pump unit 106 can be a passive device which may be entirely controlled and powered by the remote transmitter 108. The antenna 211 on the electronics board 210 is housed within the high precision pump unit 106 and the remote transmitter 108 is coupled to allow the transmission 124 of signals and power through the skin 122 (as illustrated in FIG. 1). The power issued from the remote transmitter 108 is continually monitored by a dedicated microprocessor to ensure that power transmission is minimized to the lowest level required for operation. To minimize the transmission 124 of power and to optimize the transmission 124 of command communication, the high precision pump unit 106 and the remote transmitter 108 have a channel frequency dedicated to command communication and a separate channel frequency dedicated to power transmission. The command communication can be configured, for example, to take place at about 402-406 MHz while the power transmission, for example, takes place at about 400 kHz. This command communication adheres to the frequency and power standards set by the Medical Implant Communications Service. To ensure accuracy, communication and control commands are verified by error check algorithms prior to data reporting or command implementation.

A portion of the electronics board 210 within the high precision pump unit 106 is devoted to conditioning and managing the power received at the antenna 211 or from a local battery. Communication electronics manage the bidirectional transmissions with timing verification and error checking. Controller circuits of the electronics board 210 send commands to the first valve 202, the second valve 204, the pump 206, and the pressure/flow sensor 208 and receive data back from the pressure/flow sensor 208. The electronics board 210 can be encased in a biocompatible sealant if further protection, or redundant protection, is necessary.

In one example embodiment, the systems and apparatus described herein are configured and structured to be compatible with MRI, or MRI safe, at, for example 1.5 T. In the exemplary embodiment shown, the high precision pump unit 106 is entirely inductively powered. The systems utilize no permanent magnets, no long metallic wires or leads, and a minimal or negligible amount of ferrous or ferromagnetic material. The systems are substantially free or contain substantially no ferromagnetic materials. Substantially no ferromagnetic materials refers to materials containing less than about 5%, in one embodiment, less than about 1% or 0.1% (w/w) of ferromagnetic material. The resulting systems are thus MRI safe given standard specifications regulating translational and rotational attraction, MRI heating, and imaging artifacts. In one embodiment, all materials selected for the systems are selected to be compatible and safe in an MRI environment.

Further, the inductive powering of the high precision pump unit 106 requires that energy be passed through body tissue. Since the body tissue absorbs a small amount of the energy passing through it, the heating of the tissue can be proportional to the total energy transferred. To ensure that the systems meet standards to minimize tissue heating (below 2° C. above body temperature per ISO 45652), the systems described herein have been designed to use very little power to move the fluid within the system and do not cause excessive heating of the patient's tissue.

The pressure/flow sensor 208 can monitor pressure inside the gastric band 102 as needed. Using the remote transmitter 108 to communicate with the high precision pump unit 106, a clinician can monitor pressure inside the gastric band 102, for example, in "real time" during an adjustment of the constriction within the gastric band 102. This will allow the clinician to observe the response of the gastric band 102 to a patient's adjustment. This may permit a new modality for the gastric band 102 adjustment management to monitor pressure as well as volume during an adjustment. With these new pressure sensing capabilities, the clinician can make a determination of whether there is a leak within the system (e.g., zero pressure reading) or whether there is an obstruction in the system (e.g., prolonged pressure rise).

In an example embodiment, the high precision pump unit 106 includes a first fluid line including a first pump for passing fluid in a first direction and a second fluid line in parallel with the first fluid line including a first valve and a second pump for passing fluid in an opposing direction. In another example embodiment, the second pump is not needed because the gastric band 102 provides enough pressure to move the fluid to the reservoir 104. The parallel line configuration allows for filling and draining of the gastric band 102 with a minimal number of components and minimal complexity.

The systems and apparatus described herein can achieve at least one of the following features. The total time required to complete a fill or drain of the gastric band 102 does not exceed about 10 minutes, and in one embodiment, about 5 minutes. The systems are able to adjust the volume in the gastric band 102 accurately to within about 0.1 cc or about 10%, whichever is greater. The pressure/flow sensor 208 has a resolution between about 0.010 psi to about 0.025 psi, and in one embodiment, about 0.019 psi (about 130 Pa).

In one example embodiment of the present invention, components of the systems can be replaced without replacing the entire system and subjecting patients to overly invasive surgeries to replace entire systems when a single component is defective or damaged. For example, if the high precision pump unit 106 becomes damaged, it can be replaced independently of other components. Alternatively, if the gastric band 102 becomes damaged, it can be replaced independently of other components. The same is true of the tubing 110 and the reservoir 104. Although components can be disconnected for single part replacement, components shall not become dislodged from the tubing 110 for tubing pull-off forces less than about 10 lbf, and in one embodiment, less than about 5 lbf (22.2 N).

The systems described herein meet at least one safety specification. For example, in the event of any failure of the systems, either no change in the gastric band 102 tightness or a loosening of the gastric band 102 results. Further, the high precision pump unit 106 is biocompatible for long term implantation and the remote transmitter 108 is biocompatible for transient use both per ISO 10993. The systems are designed to have no significant interaction or interference with other electronics in any of the following modalities: implantable energy sources such as defibrillators and pacemakers; internal energy sources such as electrosurgical instruments; external energy sources such as ultrasound, x-rays and defibrillators; and radiofrequency signals such as pacemaker programmers and neurostimulators.

Example 1

Implantation of a Gastric Band System

A 40 year old female is diagnosed by her clinician as obese, weighing 510 lbs. The clinician suggests to the patient that she consider the gastric banding system 100 according to the present invention. She agrees and undergoes the implantation procedure. The gastric band 102 is implanted around her cardia thereby creating a stoma. The high precision pump unit 106 is sutured onto the rectus muscle sheath and the tubing 110 and the reservoir 104 passes through the rectus muscle into the peritoneal cavity and connects to the gastric band 102. The gastric banding system 100 comes pre-filled, so there is no need for the clinician to fill the gastric banding system 100 during the surgical procedure. The patient is sutured and sent to recovery.

Example 2

Adjustment of a Gastric Band System

The female patient of Example 1, after the completion of the surgical implantation, has her gastric band system 100 properly adjusted by her clinician. The clinician holds the remote transmitter 108 to the skin 122 adjacent to the rectus muscle where the high precision pump unit 106 is located and initiates communication between the devices. An initial pressure of zero is displayed for the gastric band 102 as no fluid has been added to the gastric band 102. The clinician begins to fill the gastric band 102 using saline housed within the reservoir 104 at a rate of about 1 cc/min and the entire filling takes less than about 5 minutes.

After filling, to about 10 psi, the patient is instructed to drink a glass of water in order to properly assess the proper inflation pressure of the gastric band 102 to ensure it has not been over inflated. Upon confirmation that the gastric band 102 is properly inflated, the procedure is completed and the patient returns to her normal life.

The patient instantly notices that she is much less hungry than she previously had been and is consistently consuming less food as her appetite has been decreased. She returns to her clinician's office for a follow-up visit three months after her implantation and initial gastric band filling and she has lost 20 pounds. A year later, she has lost nearly 60 lbs.

The gastric banding system 100 generally functions as follows. When a clinician uses the remote transmitter 108 to adjust the gastric band 102, the high precision pump unit 106 initiates a sequence of events to move a precise amount of fluid in the desired direction, where the filling is discussed in FIG. 3A and the draining is discussed in FIG. 3B.

Figure 3A:
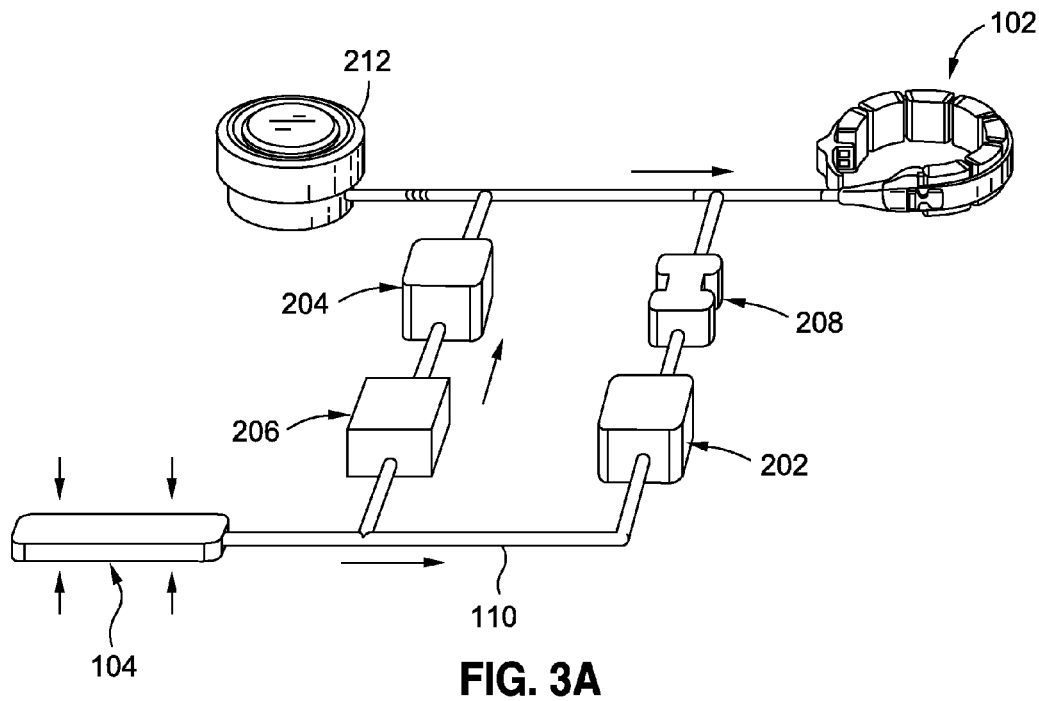
FIGS. 3A and 3B illustrate the filling and draining, respectively, of a gastric band using the systems described herein according to an embodiment of the present invention.

FIG. 3A illustrates the filling of the gastric band 102 according to an embodiment of the present invention. Just before pumping is initiated, the second valve 204, in line with the pump 206, is opened. The pump 206 creates a differential pressure to draw fluid out of the reservoir 104 and into the gastric band 102. The first valve 202 and the pressure/flow sensor 208 are closed or not engaged. The reservoir 104 is collapsible and does not impede the outward flow of fluid. Further, the reservoir 104 is sized such that when filled to the maximum recommended fill volume, there is a slight vacuum therein. Once the proper amount of fluid has been transferred from the reservoir 104 to the gastric band 102, the electronics board 210 (or circuitry thereon) shuts off the pump 206 and closes the second valve 204. The gastric band 102 now assumes the new higher pressure and fluid.

Figure 3B:
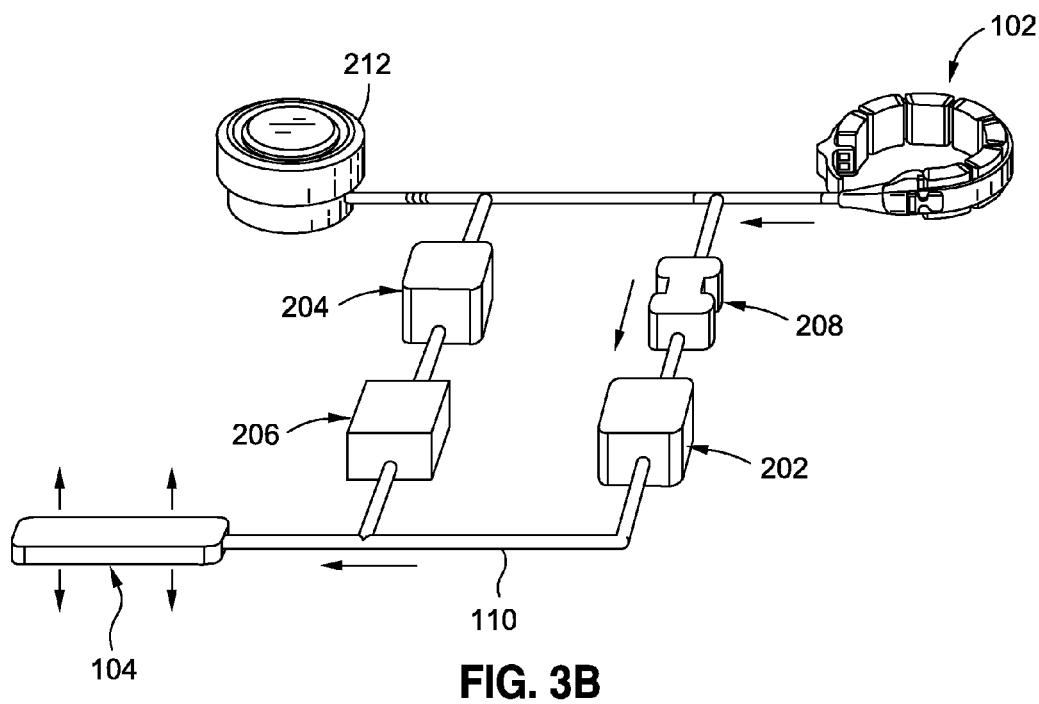

Referring to FIG. 3B, if the clinician decides that there is a need to loosen the gastric band 102, fluid is released from the gastric band 102 and returned to the reservoir 104. Once the high precision pump unit 106 receives a drain command from the remote transmitter 108, the first valve 202 behind the pressure/flow sensor 208 opens. The fluid is transferred from the gastric band 102 through the pressure/flow sensor 208 and the first valve 202 and into the reservoir 104. The amount of fluid released from the gastric band 102 can be monitored and determined by the pressure/flow sensor 208. Once the correct volume of fluid has been transferred, the first valve 202 is closed. With both the first valve 202 and the second valve 204 closed, the volume in the gastric band 102 is maintained and the pressure in the gastric band 102 can be measured accurately using the pressure/flow sensor 208.

When compared to conventional gastric banding systems having standard access ports which exclusively require syringe access (as opposed to being optional), the presently described systems and apparatus offer several benefits. First, the conventional access ports are located under a thick layer of fatty tissue, which is generally the case as the devices are generally used to treat obesity, and the access port can be difficult to locate. The present systems reduce or eliminate the need for (or to locate) the access port, as the use of the remote transmitter 108 removes the need for adjustment using the hypodermic needle 112.

Secondly, when accessing the access port in conventional systems, the ambiguity on its location may lead to damage by accidentally puncturing the tubing 110 which connects the access port 212 to the gastric band 102. This can require a revision surgery in order to repair the punctured tubing 110. Further, when a conventional access port cannot be located by palpation, x-ray imaging may be required to guide a needle into the access port. Such imaging practices put a patient at risk for x-ray radiation exposure. The present systems and apparatus remove the need for these unnecessary procedures and save the patient from x-ray radiation exposure. The present systems and apparatus are compatible with magnetic resonance imaging (MRI), which is much safer for a patient.

In the unlikely event that the override port 212 of the present invention needs to be used, the override port 212 may be located away from the tubing connection to the gastric band 102 to reduce the potential for tubing needle sticks. The high precision pump unit 106 has geometry and a rigid case that can be structured to facilitate the user in locating the override port 212 when needed.

Figure 4A:
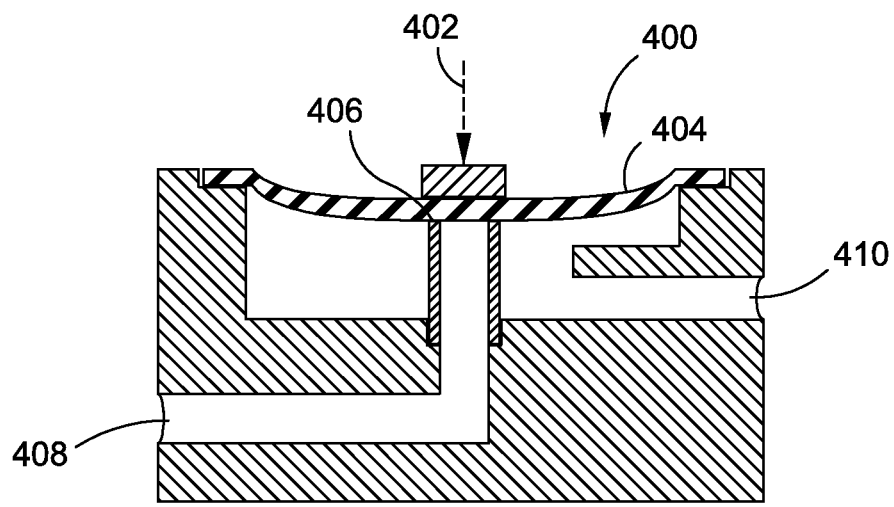
FIGS. 4A and 4B illustrate cross-sectional views of an exemplary valve in a closed position and an open position according to an embodiment of the present invention.
Figure 4B:
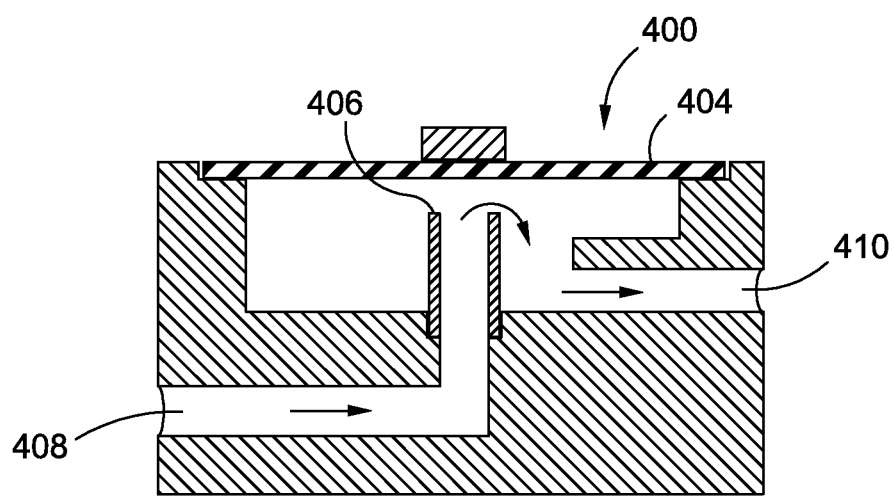

FIGS. 4A and 4B illustrate cross-sectional views of an exemplary valve 400 in a closed position (FIG. 4A) and an open position (FIG. 4B) according to an embodiment of the present invention. The valve 400 may be used in place of one or both of the first valve 202 and the second valve 204.

Referring to FIG. 4A, the valve 400 is biased in a closed position, for example, by a spring preload force 402 acting on a seal 404, for example, a flexible silicone seal 404. For example, the spring preload force 402 pushes the flexible silicone seal 404 into sealing engagement with a valve seat 406. When the valve 400 is sealed as shown in FIG. 4A, fluid cannot pass from a valve inlet 408 to a valve outlet 410.

Now referring to FIG. 4B, when fluid flow is desired, a signal is sent to a valve actuator (not shown), which removes the spring preload force 402 and permits the flexible silicone seal 404 to relax or move upward into an open position, out of sealing engagement with the valve seat 406. The fluid is then free to flow from the valve inlet 408 to the valve outlet 410 until the valve 400 is closed, for example, by reapplication of the spring preload force 402.

Figure 5A:
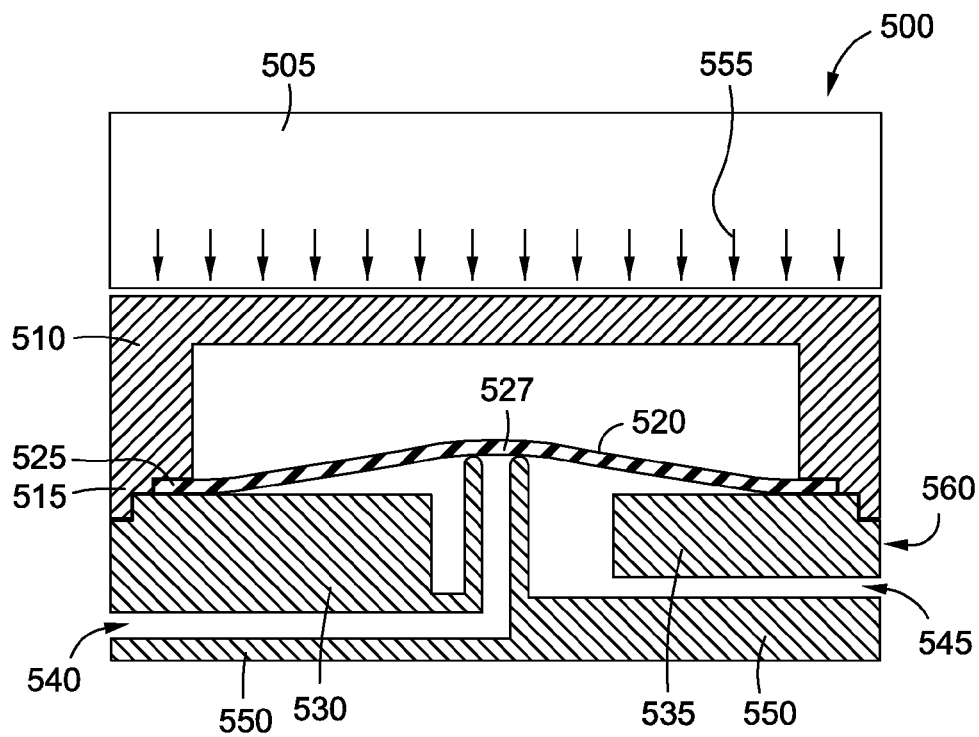
FIGS. 5A and 5B illustrate cross-sectional views of an exemplary dome valve in a closed position and an open position according to an embodiment of the present invention.
Figure 5B:
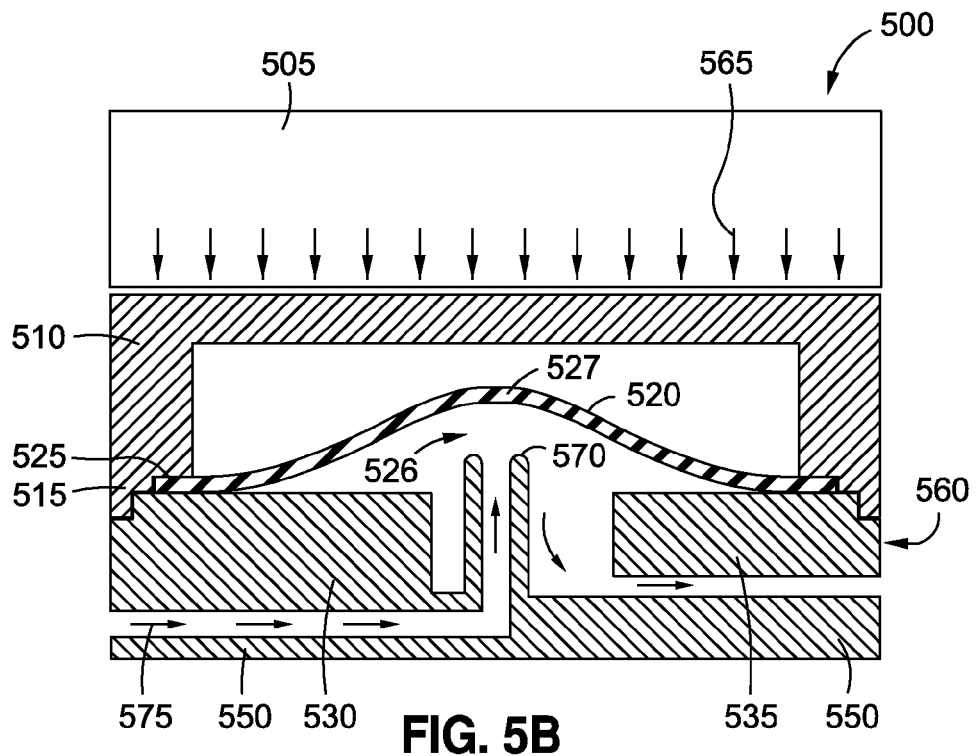

FIGS. 5A and 5B illustrate cross-sectional views of an exemplary dome valve 500 in a closed position (FIG. 5A) and an open position (FIG. 5B) according to an embodiment of the invention. In one embodiment, the dome valve 500 is an implantable device that controls the movement of fluid to the inflatable portion 114 of the gastric band 102. The dome valve 500 may be used in place of one or both of first valve 202 and the second valve 204.

The dome valve 500 is designed to be implanted into a patient, and thus may be referred to as a micro valve. In an embodiment, the dome valve 500 has a length of about 15 mm (e.g., 10-25 mm range) and an about 10 mm outer diameter (e.g., 7-15 mm range). In one embodiment, the dome valve 500 is a radially symmetric shape (e.g., disk, tube, rod, etc.). However, the dome valve 500 can be any shape (e.g., circular, square, rectangular, etc). The dome valve 500 can include a body 560, an actuator 505, a cap 510, and a diaphragm 520.

The body 560 has an inlet component 530, an outlet component 535, and a bottom component 550. The inlet component 530, the outlet component 535, and the bottom component 550 have been identified for illustrative purposes and may not be separate components from the body 560. An inlet 540, which is a fluid entrance into the body 560, is defined between the inlet component 530 and the bottom component 550. An outlet 545, which is a fluid exit from the body 560, is defined between the outlet component 535 and the bottom component 550.

The inlet component 530 and the bottom component 550 form a valve seat 570. The valve seat 570 can be the surfaces (e.g., the tips) of the inlet component 530 and the bottom component 550 which provide sealing when the diaphragm 520 is placed against and in contact with the inlet component 530 and the bottom component 550. In one embodiment, the vertical column of the inlet component 530 and the bottom component 550 define the valve seat 570. The vertical columns may be short segments (e.g., 1.5 mm) of plastic or metal tubing (e.g., stainless steel).

The actuator 505 is configured to apply a force (e.g., stress) on the cap 510 causing the diagraph 520 to move from the closed position (FIG. 5A) to the open position (FIG. 5B) when the actuator 505 receives a telemetric signal 124 (e.g., electrical energy) from the remote transmitter 108. The force includes a smaller downward force 555 to keep the valve 500 in a closed position (FIG. 5A) and a larger downward force 565 to keep the valve 500 in an open position (FIG. 5B). In an embodiment, the smaller force 555 is less than 10 newtons. In an embodiment, the larger force 565 is between 10-100 newtons. In another embodiment, the larger force 565 is between 15-45 newtons.

FIG. 5A illustrates the actuator 505 applying the smaller force 555 (e.g., 0 newtons, little or no downward force, a reduced in force, a de-energized state), which is low enough to keep the valve 500 in the closed position. In particular, when the actuator 505 applies the smaller force 555, the cap 510 receives little or no downward force on cap edges 515. Since the cap edges 515 are adjacent to the diaphragm edges 525, the diaphragm edges 525 also receive little or no downward force. As such, the diaphragm center 527 of the diaphragm 520 remains sitting on (or relaxed onto) the valve seat 570, blocking fluid from flowing from the inlet 540 to the outlet 545.

FIG. 5B illustrates the actuator 505 applying a large force 565 (e.g., an energized state) that compresses (e.g., squeezes) the diaphragm edges 525 between the cap 510 and the body 560. The large force 565 is great enough that the material on the diaphragm edges 525 is compressed, with the cap 510 blocking diaphragm edges 525 from expanding outward, the diaphragm is expanded inward such that the diaphragm center 527 is moved up off the valve seat 570 due to a build-up of material. This opens a passage from the inlet 540 to the outlet 545 and permitting fluid flow in the valve 500 as shown by fluid flow indicators 575. When a downward force is applied, the diaphragm center 527 moves in a substantially opposite direction to the downward force.

The actuator 505 can take many forms (e.g., solenoids, stepper motors, piezoelectric actuator, electroactive polymer, etc.) as dictated by the specific application. In one embodiment of the RAB, the actuator 505 is a piezoelectric actuator. In another embodiment, the actuator 505 is an electroactive polymer.

The cap 510 may be positioned between the diaphragm 520 and the actuator 505. The cap 510 has one or more cap edges 515 (e.g., cap ends). The cap edges 515 direct the small force 555 and the large force 565 from the actuator 505 to the diaphragm 520. In one embodiment, the cap 510 is part of the actuator 505.

The diaphragm 520, which may be referred to as a valve seal, is positioned between the cap 510 and the body 560. The diaphragm 520 has a diaphragm center 527 (e.g., a body) and one or more diaphragm edges 525 (e.g., ends of the diaphragm 520) coupled to the body 560.

The diaphragm 520 (e.g., valve seal) has an open position (FIG. 5B) and a closed position (FIG. 5A). When the diaphragm 520 is in the open position, the diaphragm 520 does not block the valve seat 570 and therefore allows the fluid to move from the inlet 540 to the outlet 545. Conversely, when the diaphragm 520 is in a closed position, the diaphragm 520 blocks the valve seat 570 and does not allow the fluid to move from the inlet 540 to the outlet 545.

In one embodiment, the diaphragm 520 is made of an elastomeric material. The elastomeric material includes silicon and any other material that is stretchy like a rubber band. For example, the elastomeric material includes flexible materials, naturally occurring elastic substances (e.g., natural rubber), and synthetically produced substances (e.g., silicon, butyl rubber, neoprene).

The elastomeric material can be stretched across the valve seat 570 to provide a seal and can buckle to create a gap 526 above the valve seat 570. In an embodiment, the gap 526 below the diaphragm 520 is substantially less than 1 mm off the valve seat 570. In one embodiment, the gap 526 is about 0.03 mm. In one embodiment, the range for the gap 526 is between about 0.01 mm to about 0.25 mm. In another embodiment, the range for the gap 526 is between about 0.01 mm to about 0.10 mm.

In one embodiment, the diaphragm 520 is circular, although any shape is possible (e.g., a thin strip, rectangular, etc).

The dome valve 500 has numerous advantages over conventional valves. The dome valve 500 contains no ferromagnetic material as is commonly used in conventional valves (e.g., solenoid valves). As a result, the dome valve 500 advantageously can be safely used in conjunction with magnetic resonance imaging (MRI) scanning.

Additionally, the dome valve 500 advantageously is not concentric with the diaphragm, unlike conventional valves which have a concentric shaped seal which results in high susceptibility to leakage and contamination to the moving parts of the valve.

Advantageously, both the diaphragm 520 and the cap 510 restrict fluid from contacting the moving valve components, such as the actuator 505. This allows the dome valve 500 to be used in a system where the fluid is highly corrosive to the moving parts and can be used where the moving parts rub and create contaminants that must be keep free from the fluid, because the dome valve 500 protects the moving valve components from contamination.

Dome valve 500 advantageously can be inexpensively manufactured, due partly to the mechanical linkage, while still being robust and efficient. Opening the valve 500 requires very little stroke or travel from the actuator 505 to produce a suitably large upward deflection in the diaphragm 520. In contrast, conventional valves use energy inefficient methods such as forming a seal for a valve by heating a membrane comprised of two materials with different coefficients of linear thermal expansion.

Also, the dome valve 500 achieves a low leak/leakage rate when in the closed position (e.g., closed/sealed tightly) compared to conventional valves and achieves a high flow rate when in the open position. Further, the dome valve 500 minimizes the space required for the implanted device because the dome valve 500 can be smaller than other implantable devices.

Figures 6A, 6B:
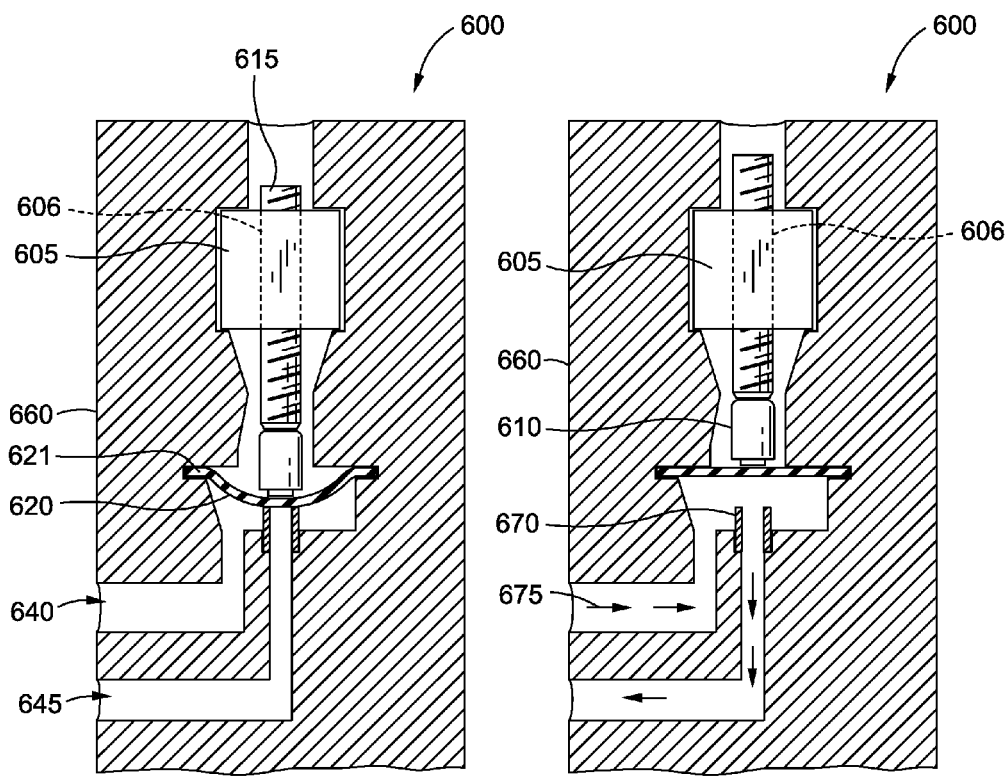
FIGS. 6A and 6B illustrate cross-sectional views of an exemplary screw valve in a closed position and an open position according to an embodiment of the present invention.

FIGS. 6A and 6B illustrate cross-sectional views of an exemplary screw valve 600 in a closed position (FIG. 6A) and an open position (FIG. 6B) according to an embodiment of the present invention. The screw valve 600 is part of the RAB and may be used in place of one or both of the first valve 202 and the second valve 204. The screw valve 600 is designed small enough to be implanted into a patient, and thus may be referred to as a micro valve. In an embodiment, the screw valve 600 has a length of approximately 30-50 mm and an about 10 mm outer diameter (e.g., 7-15 mm range). In comparison to the dome valve 500 embodiment discussed above (10-25 mm length, 10 mm outer diameter), the screw valve 600 is almost twice as long, but has the same outer diameter.

The screw valve 600 in accordance with one embodiment of the present invention generally includes a body 660, a screw 615, a screw actuator 605, a coupling mechanism 610, a valve seal 620, and a valve seat 670.

The body 660 houses the components of the screw valve 600. The body 660 also has an inlet 640 and an outlet 645. The inlet 640 may be in communication with the reservoir 104 and the outlet 645 may be in communication with the inflatable portion 114 of the gastric band 102, or vice-versa, using suitable fluid port connectors, not shown.

The screw 615 includes a lead screw (where lead means a type of screw, and does not mean the material lead as used in a graphite pencil), power screw, translation screw. The screw 615 can be designed to translate radial (e.g., circular) motion/movement into linear (e.g., translational) motion/movement. The screw 615 is configured to apply a force on the valve seal 620 to cause the valve seal 620 to move from an open position (FIG. 6B) to a closed position (FIG. 6A) when the screw actuator 605 receives a telemetric signal 124 from the remote transmitter 108.

The screw actuator 605, positioned within the body 660 of the screw valve 600, has an actuator body defining a threaded screw hole 606. The screw 615 is positioned within the threaded screw hole 606.

In one embodiment, the screw actuator 605 is a motor. In another embodiment, the motor may be positioned within the screw actuator 605. In another embodiment, the motor is external to the body 660 for moving the screw 615.

The motor (not shown) may also be included in the screw valve 600 and coupled to the screw 615 for moving the screw 615 within the threaded screw hole 606. The motor can be a DC motor, an AC motor, a solenoid, a stepper motor, a piezoelectric actuator, a piezoelectric driver, and an electroactive polymer. In one embodiment, the motor is selected to be the same type of motor used elsewhere in the implantable system.

The motor can be configured to move the screw 615 to at least two positions so that the valve seal 620 can be moved to at least two positions depending on the telemetric signal 124 sent from the remote transmitter 108 to the actuator 605.

Figure 7A:
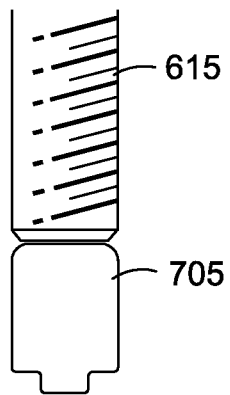
FIGS. 7A, 7B and 7C illustrate side views of examples of the coupling mechanism illustrated in FIGS. 6A and 6B according to various embodiments of the present invention.
Figure 7B:
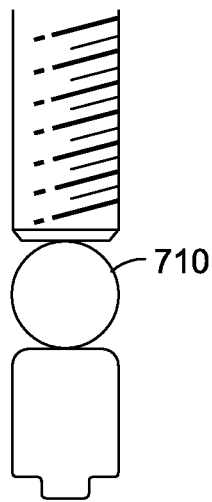
Figure 7C:
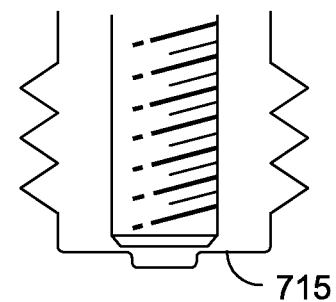

The coupling mechanism 610, positioned between the valve seal 620 and the screw 615, decouples a rotational motion of the screw 615. In one embodiment, the coupling mechanism 610 may be securely fastened or fixed to the valve seal 620 so that the coupling mechanism 610 does not rotate with the rotation of the screw 615. The screw 615 moves forward and backward (or upward and downward) through both rotational and translational motion. However, to prevent damage to the valve seal 620, the valve seal 620 should only receive translational motion (not rotational motion). The coupling mechanism 610 decouples the rotational motion of the screw 615 but transmits the translational motion. The coupling mechanism 610 is illustrated as being a tappet, but can also include a ball bearing, a bellows unit, etc., as illustrated in FIGS. 7A-7C.

The valve seal 620 has one or more edges 621 coupled to the body 660. The valve seal 620 is capable of being moved from an open position that is spaced apart from the valve seat 670 and does not block a fluid (e.g., saline) from flowing from the inlet 640 to the outlet 645 to a closed position that blocks or contacts the valve seat 670 and does not allow the fluid to move from the inlet 640 to the outlet 645. The valve seal 620 can be in the closed position, the open position, and a partially-open position, which is between the closed position and the open position.

The valve seal 620, like the diaphragm 520, is made of an elastomeric material. In one embodiment, the elastomeric material is silicon. However, any material that is stretchy like a rubber band can be used. For example, the elastomeric materials include flexible materials, naturally occurring elastic substances (e.g., natural rubber), and synthetically produced substances (e.g., silicon, butyl rubber, neoprene).

The valve seat 670 provides an opening for the valve seal 620 to close or open. To close the screw valve 600, a command signal (e.g., a telemetric signal) is sent to the screw actuator 605 which drives the screw 615 (and the coupling device or mechanism 610) into the valve seal 620 to press the valve seal 620 onto the valve seat 670. To open the screw valve 600, a command signal is sent to the screw actuator 605 which drives the screw 615 (and the coupling device or mechanism 610) away from the valve seal 620 to decompress or move the valve seal 620 away from the valve seat 670.

The pressure/flow sensor 208 may also be included in or coupled to the screw valve 600. For example, one or both of the flow sensor and/or the pressure sensor can be coupled to the valve seat 670 for determining and adjusting an amount of the fluid flowing between the inlet 640 and the outlet 645.

FIG. 6A illustrates the screw 615 displacing the valve seal 620 onto the valve seat 670 to block the fluid from flowing from the inlet 640 to the outlet 645.

FIG. 6B illustrates the screw 615 moved upward such that the valve seal 620 is not touching the valve seat 670 to allow the fluid to flow from the inlet 640 to the outlet 645 as shown by fluid flow indicators 675. The fluid can also flow in the opposite direction as shown by the fluid flow indicators 675.

The lead screw valve 600 provides many advantages when used for the gastric banding system 100. For example, the screw valve 600 achieves a low leak/leakage rate when closed (e.g., closed/sealed tightly) compared to conventional valves and a high flow rate during adjustment. The screw valve 600 is also easier to manufacture than other implantable devices (such as the dome valve 500).

An additional advantage, is that the screw valve 600 can remain in position (e.g., fully open, partially open, tightly closed) in the presence of very high constant and intermittent pressures present from the inlet 640 and the outlet 645. For example, the screw valve 600 can handle high pressures, such as 30 psi. The screw valve 600 can resist high pressures by being overdriven and by being a normally-still valve.

If the screw 615 is intentionally overdriven, the screw 615 presses tightly against the coupling mechanism 610, which presses tightly against the valve seal 620, which presses tightly against the valve seat 670. The term overdriven means that the screw 615 is driven just beyond the point where the valve seal 620 contacts the valve seat 670. The phrase "just beyond" means a point where force is generated. Even though it's not possible (without damage) to move the valve seal 620 beyond the point that it touches the valve seat 670, it is possible to generate force. For example, forces develop in the motor and forces develop loading up the motor. These forces creating a force balance between the valve seal 620 and the valve seat 670. In one embodiment, "just beyond" is a point where an additional force is required from the motor.

Even though the screw 615 drives the valve seal 620 hard into the valve seat 670, in one embodiment, the valve seal 620 is made of a soft material (e.g., silicon) and the valve seat 670 is made of a hard material (e.g., polished stainless steel) such that the two materials can be pressed together without resulting in substantial damage or marring. This tight seal blocks fluid, including fluid under high pressure. The screw 615 can optionally be reversed to relieve any unwanted excess pressure on the screw 615, the coupling mechanism 610, the valve seal 620, and the valve seat 670.

Another advantage of the screw valve 600 is that the screw 615 can resist the opening and closing in the presence of steady or high pressure, without requiring an additional energy, because the screw valve 600 is a normally still valve (as oppose to normally open or normally closed). Thus, in the absence of a drive command, the screw actuated valve will remain in whichever state it was left, whether that was fully open, partially open, or fully closed.

An additional advantage of the screw valve 600 is the amount of positions available to regulate fluid flow. The screw valve 600 can be fully open, fully closed, or anywhere in between, providing significant flexibility in designing actuation drive characteristics. The fluid flow rate can be adjusted by partially opening the screw valve 600. The screw seal 620 can occupy any position by making precise and incremental adjustments to the screw 615. In one embodiment, the screw valve 600 is used in a closed loop system, where a sensor (e.g., flow sensor, a pressure sensor, etc.) is used to adjust the position of the screw 615 to regulate the fluid flow from the inlet 640 to the outlet 645.

FIGS. 7A, 7B and 7C illustrate side views of examples of the coupling mechanism 610 illustrated in FIG. 6 according to various embodiments of the present invention. FIG. 7A illustrates a tappet 705 as the coupling mechanism 610. The tappet 705 can be a sliding rod for moving a valve. The tappet 705 touches the screw 615, and connects or rides on the screw 615. The tappet 705 allows an intentional rotational slippage between the tappet 705 and the screw 615 to decouple the rotational motion.

FIG. 7B illustrates a ball 710 along with the tappet 705 as the coupling mechanism 610. The ball 710 is located between the screw 615 and the tappet 705. The ball 710 provides two surfaces designed to allow an intentional rotational slippage between the screw 615 and the valve seal 620. Having two surfaces for slippage is advantageous because one surface may bind-up due to particulate contamination (e.g., particles from the screw 615 or the tappet 705) or manufacturing imperfection (e.g., molding flash, burrs, etc.). The ball 710 can be a ball bearing.

FIG. 7C illustrates a bellows unit 715 as the coupling mechanism 610 used with the screw 615. The bellows unit 715 can isolate the screw 615 from the valve seal 620. Without the bellows unit 715, the screw 615 would rotate and rub against a surface of the valve seal 620 generating particulates which are further rubbed against the valve seal 620. Since the valve seal 620 can be sensitive and not designed to be rubbed with particulates, the bellows unit 715 advantageously keeps all the possible generated particulates enclosed and sealed away from the valve seal 620.

Figure 8:
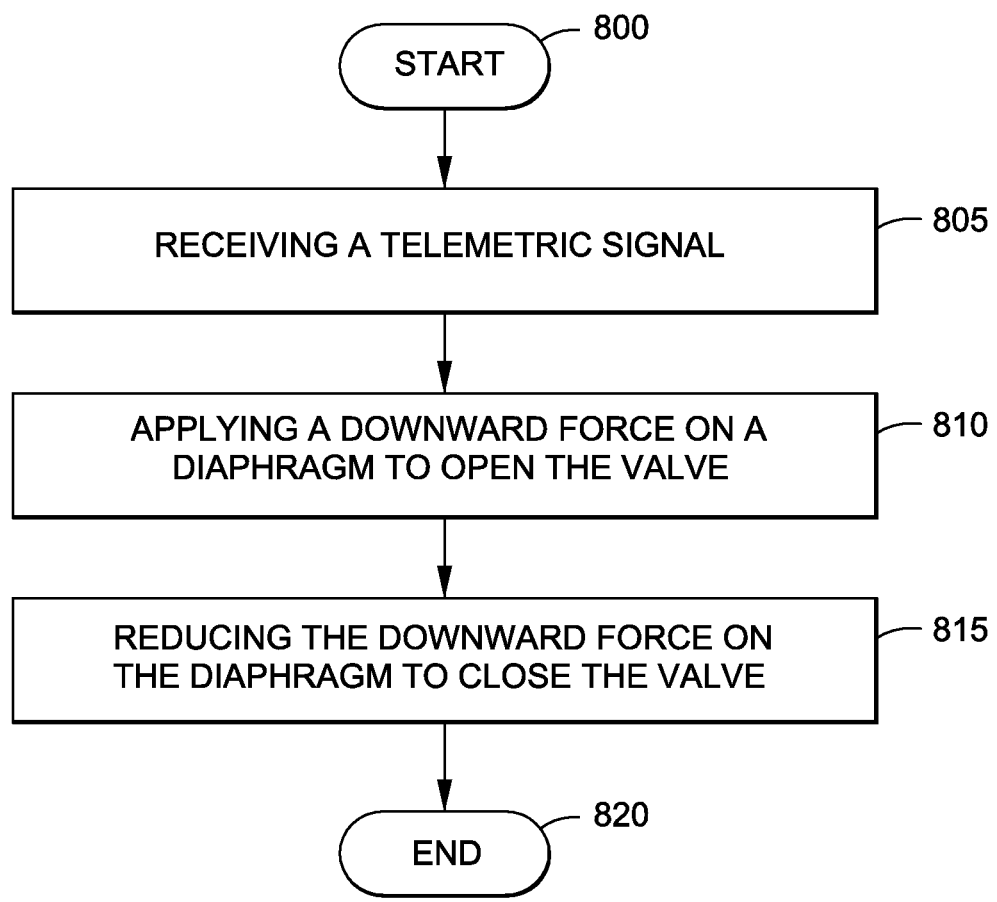
FIG. 8 is a flow chart of a method of controlling a dome valve according to an embodiment of the present invention.

FIG. 8 is a flow chart of a method of using the dome valve 500 to control the movement of fluid between the reservoir 104 and the inflatable portion 114 of the gastric band 102.

The process starts at step 800. At step 805, the dome valve 500 receives a telemetric signal from the remote transmitter 108. Alternatively, the dome valve 500 can receive a signal from an implanted microcontroller. The implanted microcontroller may be part of, coupled to or located within the actuator 505. The implanted microcontroller can receive a telemetric signal from the remote transmitter 108. Next, the actuator 505 applies a downward force on the diaphragm 520 to open the dome valve 500 at step 810. The downward force is applied onto the diaphragm edges 525 of the diaphragm 520 in the dome valve 500, lifting up the diaphragm center 527, and allowing fluid to flow through the dome valve 500.

At step 815, the actuator 505 reduces the downward force on the diaphragm 520 to close the dome valve 500. The downward force is reduced on the diaphragm edges 525 of the diaphragm 520 in the dome valve 500, lowering the diaphragm center 527, and blocking fluid from flowing through the dome valve 500. The process ends at step 820.

Figure 9:
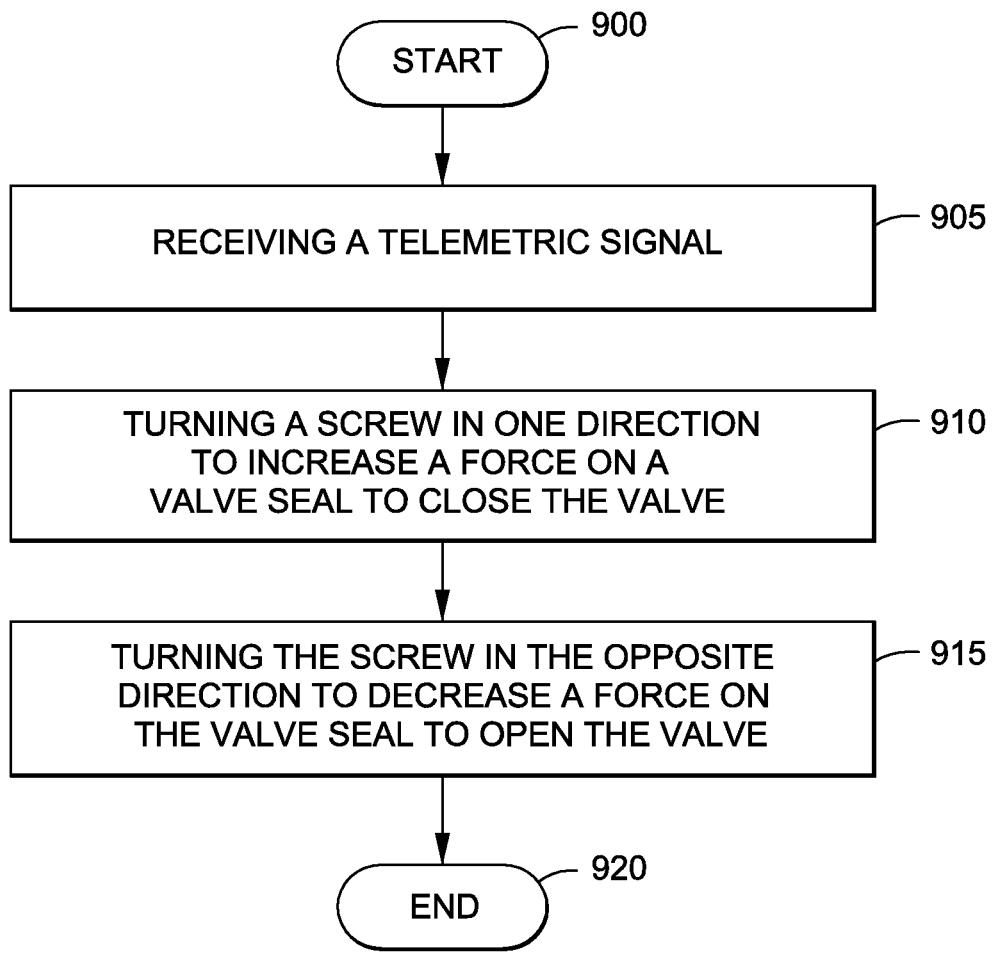
FIG. 9 is a flow chart of a method of controlling a screw valve according to an embodiment of the present invention.

FIG. 9 is a flow chart of a method of using the screw valve 600 to control the movement of fluid between the reservoir 104 and the inflatable portion 114 of the gastric band 102.

The process starts at step 900. At step 905, the screw valve 600 receives a telemetric signal from the remote transmitter 108. Alternatively, the dome valve 600 can receive a signal from an implanted microcontroller. The implanted microcontroller may be part of, coupled to or located within the screw actuator 605. The implanted microcontroller can receive a telemetric signal from the remote transmitter 108. At step 910, the screw actuator 605 turns the screw 615 in one direction to increase a force on the valve seal 620 to close the screw valve 600.

Then, the screw actuator 605 turns the screw 615 in the opposite direction to decrease the force on the valve seal 620 to open the screw valve 600. The process ends at step 920.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of the present invention are described herein, including the best mode known to the inventors for carrying out the present invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, the present invention includes all modifications and equivalents of the subject matter recited in the claims appended hereto as permitted by applicable law. Moreover, any combination of the above-described elements in all possible variations thereof is encompassed by the present invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. An implantable device for controlling movement of a fluid to an inflatable portion of a gastric band, the implantable device comprising:
   - a body having an inlet, an outlet and a single valve seat positioned between the inlet and the outlet, the valve seat being in fluid communication with the inlet and the outlet, the body defining a fluid passage from the inlet to the outlet;
   - a diaphragm having one or more edges coupled to the body, the diaphragm being made of an elastomeric material, wherein the diaphragm is directly seated on the valve seat in a closed position that blocks the valve seat and blocks fluid communication between the inlet and the outlet, and wherein the diaphragm is not seated on the valve seat in an open position that does not block the valve seat and does not block fluid communication between the inlet and the outlet;
   - an actuator configured to apply a downward force, in a direction from the diaphragm toward the valve seat, on the diaphragm causing the diaphragm to move from the closed position to the open position; and
   - a microcontroller coupled to the actuator, the microcontroller configured to receive a telemetric signal from a remote transmitter and control the actuator based on the telemetric signal.

2. The implantable device of claim 1 further comprising a cap, coupled between the diaphragm and the actuator, for directing the force from the actuator to the diaphragm.

3. The implantable device of claim 1 wherein the force is applied on the one or more edges of the diaphragm.

4. The implantable device of claim 1 wherein the diaphragm prevents the fluid from coming into direct contact with the actuator.

5. The implantable device of claim 1 wherein the diaphragm is made of a flexible material.

6. The implantable device of claim 1 wherein the diaphragm is in the open position when the actuator is in an energized state.

7. The implantable device of claim 1 wherein the diaphragm is in the closed position when the actuator is in an unenergized state.

8. The implantable device of claim 1 wherein the actuator is selected from a group consisting of a solenoid, a stepper motor, a piezoelectric actuator, an electroactive polymer, and combinations thereof.

9. The implantable device of claim 1 wherein the remote transmitter transmits the telemetric signal to the microcontroller.

* * * * *